(12) United States Patent
Hunt et al.

(10) Patent No.: US 8,012,097 B1
(45) Date of Patent: *Sep. 6, 2011

(54) MONITORING DEVICE FOR AN INTERACTIVE GAME

(75) Inventors: Mark Hunt, San Diego, CA (US);
Nikolai Rulkov, San Diego, CA (US);
Donald Brady, Las Vegas, NV (US)

(73) Assignee: Impact Sports Technologies, Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/021,749

(22) Filed: Feb. 5, 2011

Related U.S. Application Data

(63) Continuation of application No. 12/838,450, filed on Jul. 17, 2010, now Pat. No. 7,892,178.

(60) Provisional application No. 61/246,522, filed on Sep. 28, 2009.

(51) Int. Cl.
*A61B 5/02* (2006.01)
*A61B 5/103* (2006.01)
*A63F 13/06* (2006.01)

(52) U.S. Cl. ........ 600/500; 600/595; 600/504; 600/479; 463/36; 463/39

(58) Field of Classification Search .......... 600/481, 600/483–507, 595; 463/36, 37, 39
See application file for complete search history.

(56) References Cited

U.S. PATENT DOCUMENTS

| | | | |
|---|---|---|---|
| 4,542,897 A * | 9/1985 | Melton et al. | 463/7 |
| 5,453,758 A * | 9/1995 | Sato | 345/158 |
| 6,026,322 A * | 2/2000 | Korenman et al. | 600/547 |
| 6,028,593 A * | 2/2000 | Rosenberg et al. | 345/156 |
| 6,190,314 B1 | 2/2001 | Ark et al. | |
| 6,366,272 B1 * | 4/2002 | Rosenberg et al. | 345/156 |
| 6,616,613 B1 * | 9/2003 | Goodman | 600/504 |
| 7,431,696 B1 | 10/2008 | Brady et al. | |
| 7,625,285 B2 | 12/2009 | Breving | |
| 7,654,901 B2 | 2/2010 | Breving | |
| 2001/0011224 A1* | 8/2001 | Brown | 705/4 |
| 2005/0059895 A1* | 3/2005 | Brown | 600/481 |
| 2006/0195291 A1 | 8/2006 | Krumm | |
| 2007/0149282 A1 | 6/2007 | Lu et al. | |

FOREIGN PATENT DOCUMENTS

WO WO2009037654 3/2009

* cited by examiner

*Primary Examiner* — Navin Natnithithadha
(74) *Attorney, Agent, or Firm* — Clause Eight IPS; Michael Catania

(57) ABSTRACT

A system and method (1000) for an interactive game is disclosed herein. The system (1000) preferably includes monitoring device (20) monitoring the vital signs of a user, and a computer (1420). The monitoring device (20) is preferably an article (25) having an optical sensor (30) and a circuitry assembly (35), and a pair of straps (26a and 26b). The monitoring device (20) preferably provides for the display of the following information about the user: pulse rate; blood oxygenation levels; calories expended by the user of a pre-set time period; target zones of activity; time; distance traveled; and/or dynamic blood pressure. The article (25) is preferably a band worn on a user's wrist, arm or ankle.

2 Claims, 22 Drawing Sheets

MONITORING DEVICE FOR AN INTERACTIVE GAME

CROSS REFERENCES TO RELATED APPLICATIONS

The Present application is a continuation-in-part application of U.S. patent application Ser. No. 12/838,450, filed Jul. 17, 2010, which claims priority to U.S. Provisional Patent Application No. 61/246,522, filed on Sep. 28, 2009, now abandoned, both of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention is related to real-time vital sign monitoring devices. More specifically, the present invention relates to a system for monitoring a user's vital signs while playing an online interactive game on a computer.

2. Description of the Related Art

There is a need to know how one is doing from a health perspective. In some individuals, there is a daily, even hourly, need to know one's health. The prior art has provided some devices to meet this need.

One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

In monitoring one's health there is a constant need to know how many calories have been expended whether exercising or going about one's daily routine. A calorie is a measure of heat, generated when energy is produced in our bodies. The amount of calories burned during exercise is a measure of the total amount of energy used during a workout. This can be important, since increased energy usage through exercise helps reduce body fat. There are several means to measure this expenditure of energy. To calculate the calories burned during exercise one multiplies the intensity level of the exercise by one's body weight (in kilograms). This provides the amount of calories burned in an hour. A unit of measurement called a MET is used to rate the intensity of an exercise. One MET is equal to the amount of energy expended at rest.

For example, the intensity of walking 3 miles per hour ("mph") is about 3.3 METS. At this speed, a person who weighs 132 pounds (60 kilograms) will burn about 200 calories per hour (60×3.3=198).

The computer controls in higher-quality exercise equipment can provide a calculation of how many calories are burned by an individual using the equipment. Based on the workload, the computer controls of the equipment calculate exercise intensity and calories burned according to established formulae.

The readings provided by equipment are only accurate if one is able to input one's body weight. If the machine does not allow this, then the "calories per hour" or "calories used" displays are only approximations. The machines have built-in standard weights (usually 174 pounds) that are used when there is no specific user weight.

There are devices that utilize a watch-type monitor to provide the wearer with heart rate as measured by a heartbeat sensor in a chest belt.

However, the prior art devices often suffer from noise, light and motion related problems. These problems are increased when the user participates in an athletic activity such as running. Further, attempting to correct one problem often creates additional problems such as increasing a sensor output which results in a shorter battery life.

The prior art has failed to provide a means for including a player's vital sign information in an interactive game, especially heart rate due to the motion problems associated with obtaining a reliable heart rate from an individual playing, exercising or in some manner moving. Thus, there is a need for a monitoring device that can be worn to provide vital sign information for a player of an interactive game.

BRIEF SUMMARY OF THE INVENTION

The present invention provides a solution to the shortcomings of the prior art. The present invention is accurate, comfortable to wear by a user for extended time periods, is light weight, and provides reliable real-time vital sign information about a player while the player is playing an interactive game.

One aspect of the present invention is a system for a playing an online interactive video game. The system preferably includes a computer and a monitoring device. The computer comprises a display screen, a short range wireless transceiver and a processor. The computer displays an interactive video game. The computer is preferably connected to a network such as the Internet, either over a wireless connection or a wired connection. The monitoring device monitors at least a real-time heart rate of the player. The monitoring device is in wireless communication with the computer through the wireless transceiver to allow the real-time heart rate of the player to be utilized in the interactive video game. The monitoring device preferably comprises an article, a processor, an optical sensor, a motion sensor, a wireless transceiver and a power source. The article has an interior surface and an exterior surface. The processor is disposed within the article. The optical sensor is positioned on the interior surface of the article. The optical sensor measures blood flow through an artery of an arm of the player. The motion sensor is disposed within the article. The motion sensor and the optical sensor are electrically connected to the processor. The processor is configured to determine the real-time heart rate of the player based on the blood flow through the artery of the player and the processor is configured to detect motion of the player based on a signal from the motion sensor. The power source provides power to the processor, the optical sensor and the motion sensor. An activity of the representation of the player on the computer is partially controlled by the real-time heart rate of the player monitored by the optical sensor and the motion of the player detected by the motion sensor.

Yet another aspect of the present invention is a system for real time monitoring of a user's vital sign during a live event within a playing environment. The system includes a monitoring device, a computing device with an electro-optical display. The monitoring device is attached to an arm, wrist or ankle of the user. The monitoring device comprises means for generating a real-time vital sign signal corresponding to the heart rate of the user, and means for transmitting the real-time vital sign signal outside of the playing environment. The computing device is positioned outside of the playing environment. The computing device comprises means for receiving the real-time vital sign signal from the monitoring device, and means for processing the real-time vital sign signal for transmission to and image on the electro-optical display.

Yet another aspect of the present invention is a monitoring device for monitoring the health of a user. The monitoring device includes an article to be worn on the user's wrist, arm or ankle. The monitoring device also includes an optical sensor, a circuitry assembly, a display member and a control component. The optical sensor is disposed on the interior surface of the article. The circuitry assembly is preferably embedded within the annular body of the article. The display member is preferably attached to an exterior surface of the annular body of the article. The control component is disposed on the exterior surface of the annular body of the article. The control component controls the input of information and the output of information displayed on the display member.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
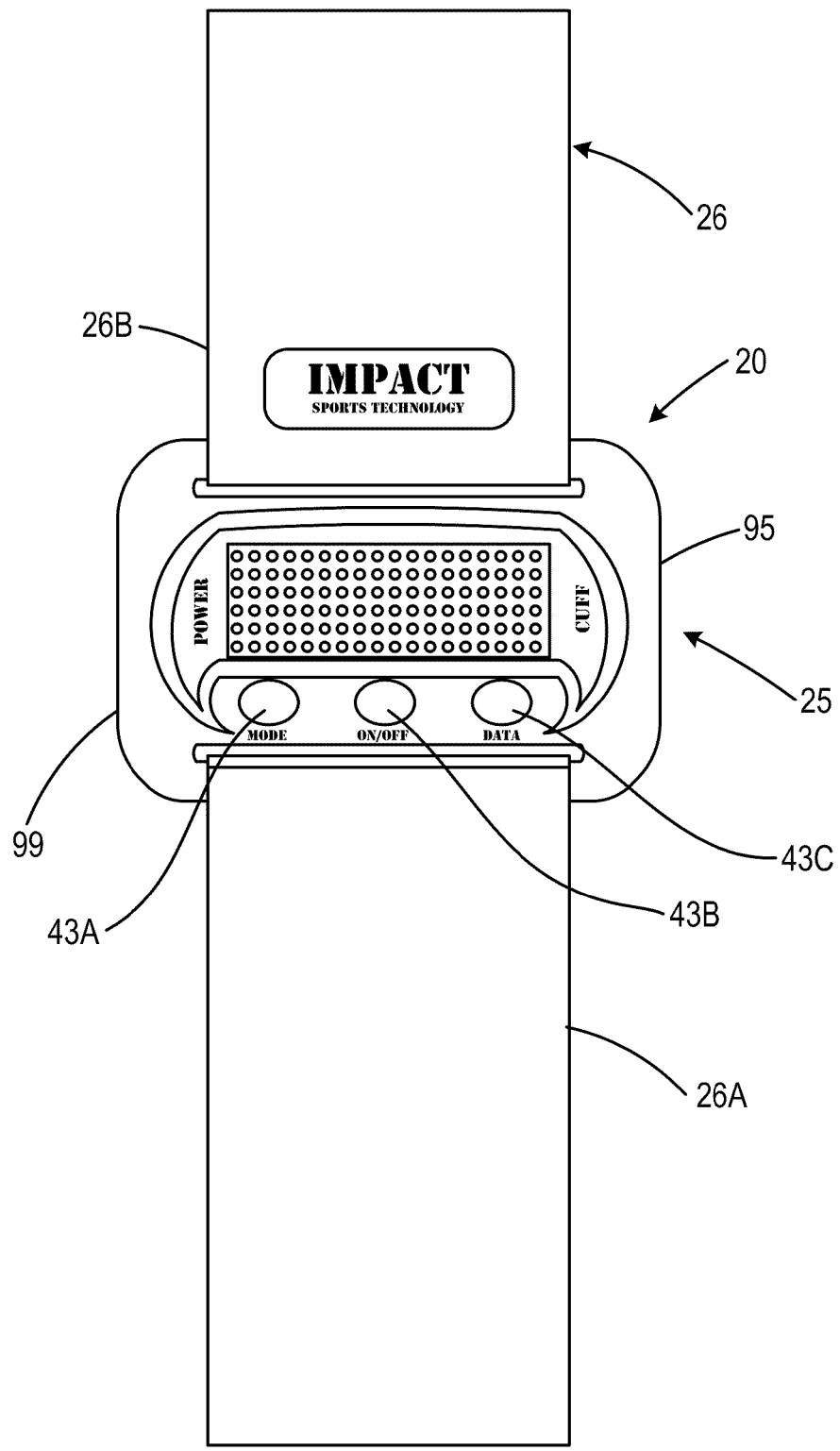
FIG. 1 is a plan view of a preferred embodiment of a monitoring device worn by a user.
Figure 2:
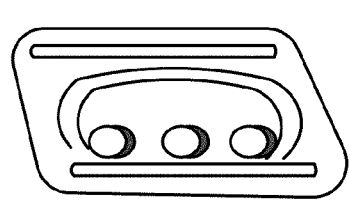
FIG. 2 is a perspective view of the article of the monitoring device worn by a user.
Figure 2A:
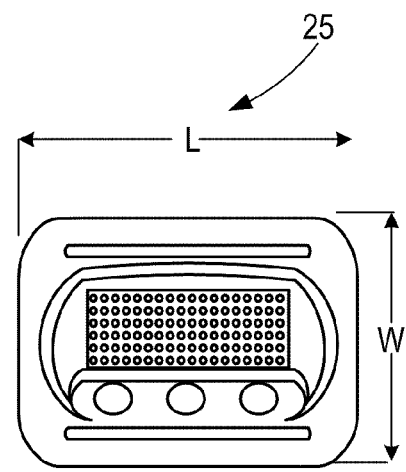
FIG. 2A is a plan view of the article of the monitoring device.
Figure 2B:
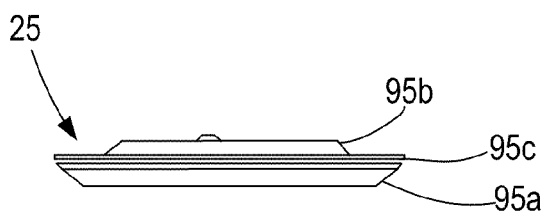
FIG. 2B is a front side view of the article of the monitoring device.
Figure 2D:
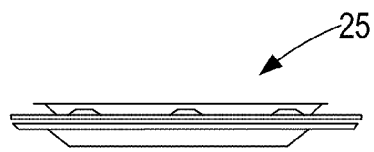
FIG. 2D is an edge side view of the article of the monitoring device.
Figure 2C:
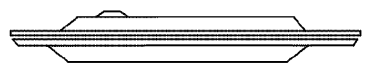
FIG. 2C is a rear side view of the article of the monitoring device.
Figure 2E:
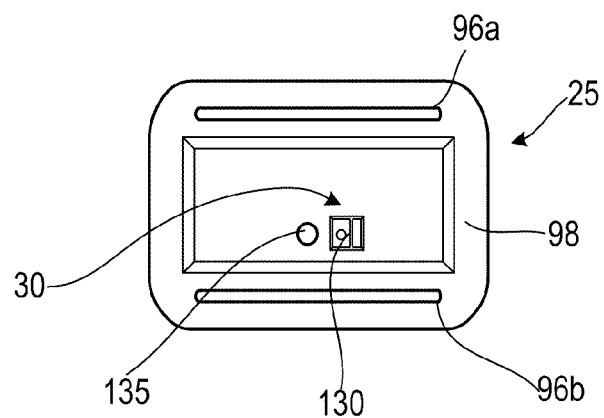
FIG. 2E is a bottom plan view of the article of the monitoring device.

As shown in FIGS. 1-2E, a monitoring device is generally designated 20. The monitoring device 20 preferably includes an article 25 and an attachment band 26, preferably composed of first strap 26a and second strap 26b. The straps 26a and 26b are preferably attached to each other with a VELCRO® hook and loop material. The article 25 preferably includes an optical sensor 30, a circuitry assembly 35, control components 43a-43c and optionally a display member 40. The monitoring device 20 is preferably worn on a user's wrist 71, arm 72 or ankle 73. The article 25 preferably has a housing 95 that is sized to securely attach to a user's wrist 71, arm 72 or ankle 73, and the housing 95 has an interior surface 98 and an exterior surface 99. The housing 95 also preferably has a pair of slots 96a and 96b for placement of the straps 96a and 96b therethrough for attachment purposes.

It is desirous to adapt the monitoring device 20 to the anatomy of the user's arm 72 or even the user's ankle, not shown. The strap 96 is preferably composed of neoprene, leather, synthetic leather, LYCRA, another similar material, or a combination thereof. The article 25 is preferably composed of a semi-rigid or rigid plastic with a rubber-like or semi-flex plastic bottom layer for contact with the user's body. Alternatively, the bottom layer of the housing 95 has a curve surface for conformance to a user's body. The article 25 preferably has a mass ranging from 5 grams to 50 grams. Preferably, the lower the mass of the article 25, the more comfort to the user. The article 25 preferably has a thickness ranging from 5 mm to 10 mm, and is most preferably 6.5 mm. The bottom layer 95a preferably has a thickness ranging from 3.0 mm to 5.0 mm, and most preferably is 3.3 mm. A top layer 95a preferably has a thickness ranging from 2.0 mm to 5.0 mm, and most preferably is 2.63 mm. A mid-layer 95c preferably has a thickness ranging from 0.25 mm to 1.0 mm, and most preferably is 0.5 mm. The housing 95 preferably has a width, W, ranging from 30 mm to 50 mm, more preferably from 35 mm to 45 mm, and is most preferably approximately 40 mm. The housing 95 preferably has a length, L, ranging from 40 mm to 65 mm, more preferably from 50 mm to 60 mm, and is most preferably approximately 55 mm. The article 25 preferably has a mass ranging from 5 grams to 50 grams, and more preferably from 10 grams to 40 grams. The light weight of the article 25 provides for more comfort when worn by a user. The optical sensor 30 is preferably positioned on the interior surface 98 of the housing 95 and is electrically connected to the circuitry assembly 35.

Although the monitoring device 20 is described in reference to an article worn on a user's arm, wrist or ankle, those skilled in the pertinent art will recognize that the monitoring device 20 may take other forms such as eyewear disclosed in U.S. Pat. No. 7,648,463, which is hereby incorporated by reference in its entirety or a glove such as disclosed in U.S. patent application Ser. No. 11/473,641, which is hereby incorporated by reference in its entirety.

Figure 4:
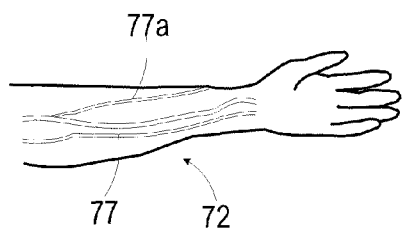
FIG. 4 is a schematic view of arteries within a human arm.

The optical sensor 30 of the monitoring device 20 is preferably positioned over the radial artery 77 or ulnar artery 77a (as shown in FIG. 4) if the article 25 is worn on the user's arm 72. The optical sensor 30 of the monitoring device 20 is preferably positioned over the posterior tibial artery of a user if the article 25 is worn on the user's ankle. However, those skilled in the pertinent art will recognize that the optical sensor may be placed over other arteries of the user without departing from the scope and spirit of the present invention. Further, the optical sensor 30 need only be in proximity to an artery of the user in order to obtain a reading or signal.

In a preferred embodiment, the optical sensor 30 is a plurality of light emitting diodes ("LED") 135 based on green light wherein the LEDs 135 generate green light (wavelength of 500-570 nm), and a photodetector 130 detects the green light. Yet in an alternative embodiment, the optical sensor 30 is a photodetector 130 and a single LED 135 transmitting light at a wavelength of approximately 900 nanometers as a pulsed infrared LED. Yet further, the optical sensor is a combination of a green light LED and a pulsed infrared LED to offset noise affects of ambient light and sunlight. As the heart pumps blood through the arteries in the user's arm, ankle or wrist, the photodetector 130, which is typically a photodiode, detects reflectance/transmission at the wavelengths (green, red or infrared), and in response generates a radiation-induced signal. A green light illuminates a user's veins and provides more motion resistance since a green light does not transmit that deeply into a user's skin which results in less motion.

A preferred optical sensor 30 utilizing green light is a TRS1755 sensor from TAOS, Inc of Plano Tex. The TRS1755 comprises a green LED light source (567 nm wavelength) and a light-to-voltage converter. The output voltage is directly proportional to the reflected light intensity. Another preferred photodetector 130 is a light-to-voltage photodetector such as the TSL260R and TSL261, TSL261R photodetectors available from TAOS, Inc of Plano Tex. Alternatively, the photodetector 130 is a light-to-frequency photodetector such as the TSL245R, which is also available from TAOS, Inc. The light-to-voltage photodetectors have an integrated transimpedance amplifier on a single monolithic integrated circuit, which reduces the need for ambient light filtering. The TSL261 photodetector preferably operates at a wavelength greater than 750 nanometers, and optimally at 940 nanometers, which would preferably have a LED that radiates light at those wavelengths.

In a preferred embodiment, the circuit assembly 35 is flexible to allow for the contour of the user's arm, wrist or ankle, and the movement thereof. The circuitry assembly and display member 40 are preferably separate components electrically connected within the housing 95. In a preferred embodiment, discussed below, the display member 40 is absent from the monitoring device 20 and the signal is sent to a device such as a television, game console, personal digital assistant, computer, mobile telephone, exercise equipment, or the like for display and even processing of the user's real-time vital signs information. Alternatively, the circuitry assembly 35 includes a flexible microprocessor board which is a low power, micro-size easily integrated board which provides blood oxygenation level, pulse rate (heart rate), signal strength bargraph, plethysmogram and status bits data. The microprocessor can also store data. The microprocessor can process the data to display pulse rate, blood oxygenation levels, calories expended by the user of a pre-set time period, target zone activity, time and dynamic blood pressure. Further, microprocessor preferably includes an automatic gain control for preventing saturation of the photodetector, which allows for the device to be used on different portions of the human body.

Figure 8:
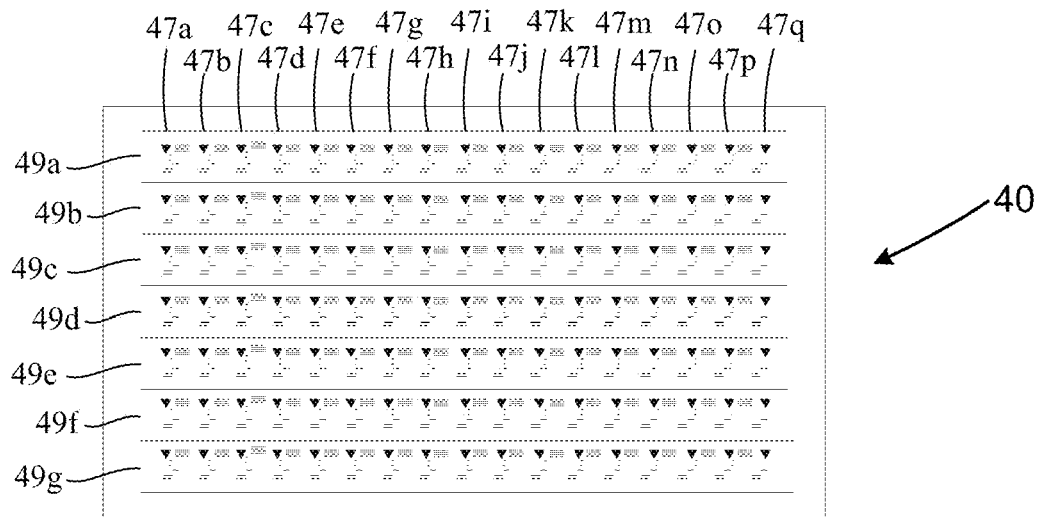
FIG. 8 is a schematic view of the display member circuitry.

The optional display member 40 is preferably a light emitting diode ("LED"). Alternatively, the display member 40 is a liquid crystal display ("LCD") or other similar display device. As shown in FIG. 8, the display member 40 is an LED array which preferably has seven rows 49a-49g and seventeen columns 47a-47q. Further, LED array is angled to allow for a greater aspect ratio. The LED array allows for each column to be illuminated separately thereby giving the appearance of a moving display. For example, if the term "200 calories expended" is displayed on the display member 40, the "2" of the "200" would preferably first appear in column 47q and then subsequently in each of the other columns 47p-47a, from the right-most column to the left-most column thereby giving the appearance of the term scrolling along the display member 40. The terms or words alternatively scroll from left to right. Still alternatively, all of the columns are illuminated at once or all flash in strobe like manner. Further, the user's real-time pulse waveform is displayed in motion on the display member 40 as a default setting. Those skilled in the pertinent art will recognize alternative methods of displaying information on the display member 40 without departing from the scope and spirit of the present invention.

Figure 9:
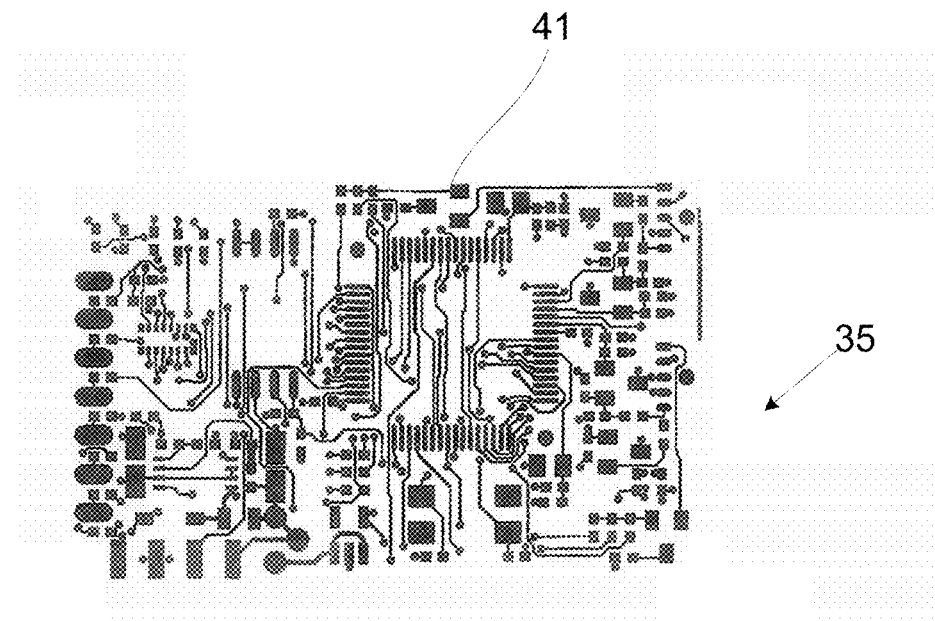
FIG. 9 is a schematic view of the circuitry assembly.

As shown in FIG. 9, a microprocessor 41 processes the signal generated from the optical sensor 30 to generate the plurality of vital sign information for the user which is displayed on the display member 40. The control components 43a-c are connected to the circuit assembly 35 to control the input of information and the output of information displayed on the display member 40.

The monitoring device 20 is preferably powered by a power source 360 positioned on the article 25. Preferably the power source is a battery. The power source 360 is preferably connected to the circuit assembly 35 by positive wire 45*a* and ground wire 45*b*, and the ground wire 45*b* and positive wire 45*c* are embedded within the article 25. The power source 360 is preferably an AA or AAA disposable or rechargeable battery. The power source 360 is alternatively a lithium ion rechargeable battery such as available from NEC-Tokin. The power source 360 preferably has an accessible port for recharging. The circuit assembly 35 preferably requires 5 volts and draws a current of 20-to 40 milliamps. The power source 360 preferably provides at least 900 milliamp hours of power to the monitoring device 20.

Figure 3:
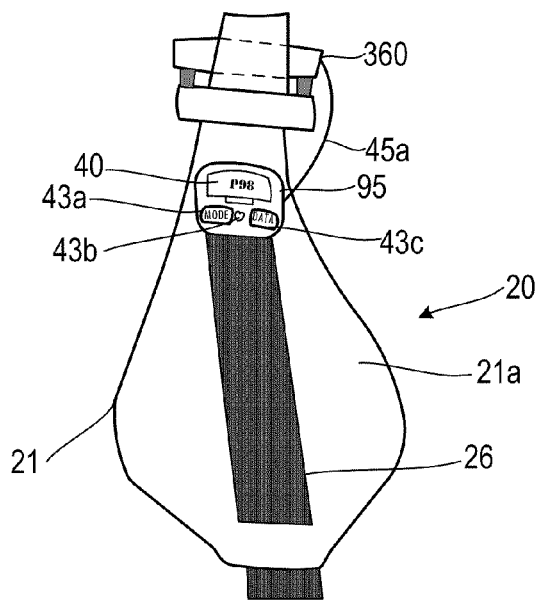
FIG. 3 is a top view of an alternative embodiment of the monitoring device of the present invention.
Figure 3A:
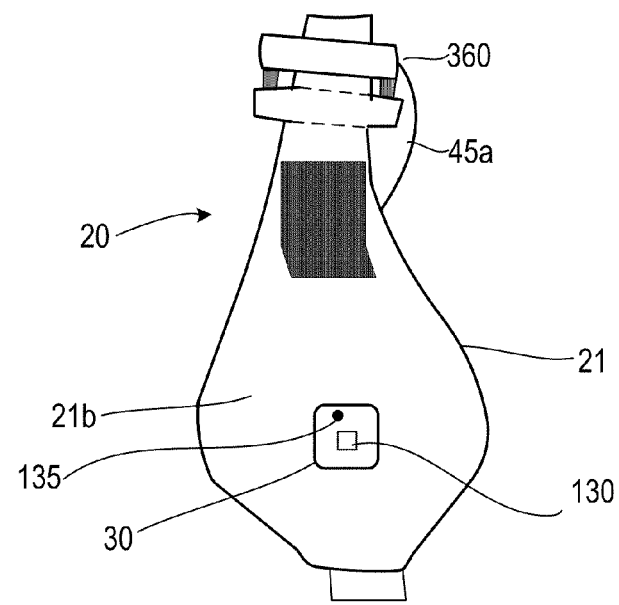
FIG. 3A is bottom view of the monitoring device of FIG. 3.
Figure 3B:
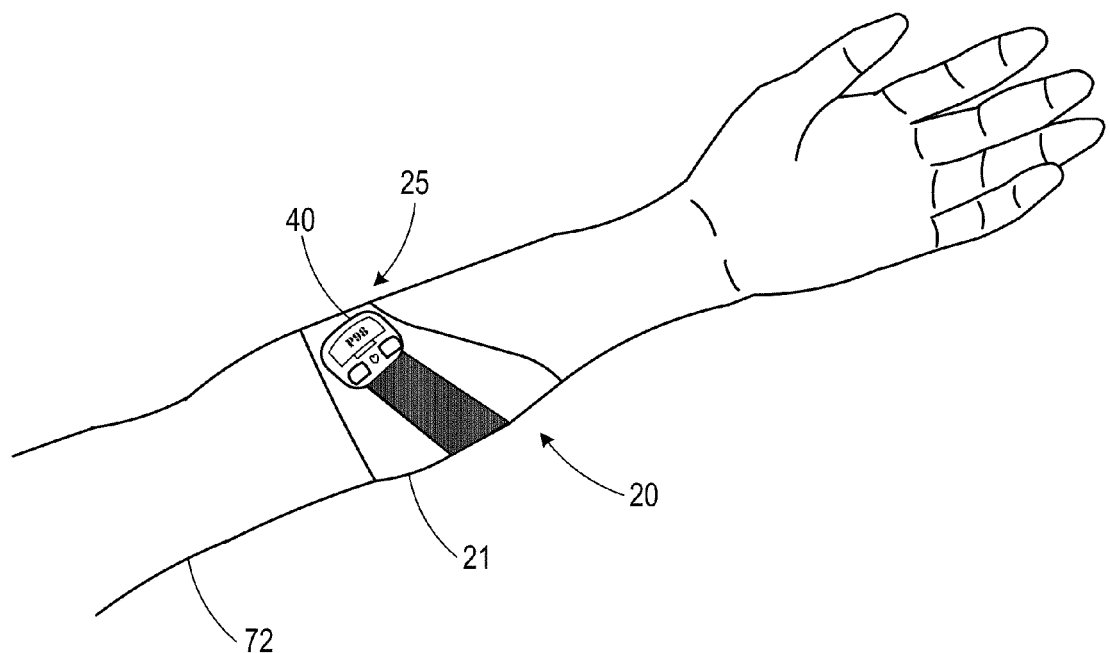
FIG. 3B is a top perspective view of the monitoring device of FIG. 3 worn on a user's arm.

As shown in FIGS. 3, 3A and 3B, an alternative embodiment of the monitoring device 20 comprises a light shield 21 with the article 25 disposed on an exterior surface 21*a* of the light shield 21, and the optical sensor 30 disposed on an interior surface 21*b* of the light shield 21. The light shield 21 is preferably composed of a light-weight, non-transparent (preferably opaque) cloth material. The light shield 21 prevents or substantially eliminates environmental light from interfering with the optical sensor 30 thereby reducing interference with the signal. In a preferred embodiment, the light shield 21 is black in color. A user preferably wears the monitoring device 20 on the user's arm 72 as shown in FIG. 3B, with a display member 40 visible to the user. In this embodiment, the article 25 contains a circuitry assembly 35, as discussed above, within the housing 95 of the article 25. The display member 40 is preferably a LED display monitor, and alternatively a LCD display monitor.

Figure 15:
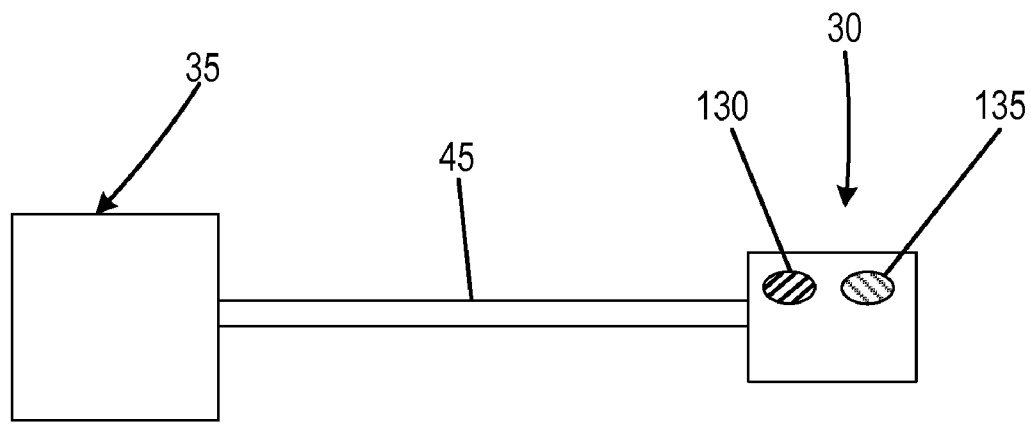
FIG. 15 is a schematic diagram of a prior art connection of a processor to an optical sensor.
Figure 16:
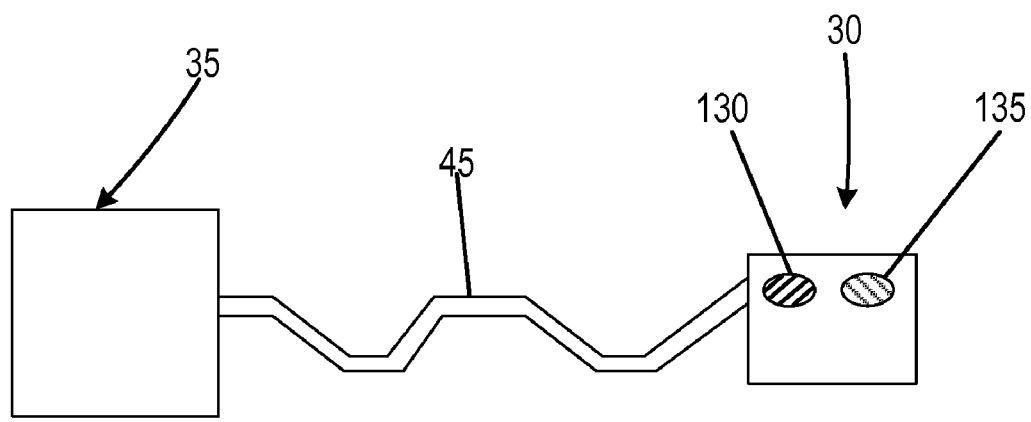
FIG. 16 is a schematic diagram of a connection of a processor to an optical sensor utilized by the present invention.

A connection wire arrangement 45 is shown in FIG. 16, wherein the connection 45 between the microprocessor 41 of the circuitry assembly 35 and the optical sensor 30 is preferably non-planar or non-straight in order to reduce noise in the signal. The optical sensor 30 preferably comprises a photodetector 130, and first and second LEDs 130*a* and 130*b*, which transmit light 137. Using two LEDs on each side of a photodetector creates a more mechanically stable optical sensor 30. The prior art connection assembly is shown in FIG. 15 wherein the connection wire 45' is straight and prone to noise due to movement of the circuitry assembly 35 relative to the optical sensor 30, especially lateral movement. The present invention has a non-straight or non-planar connection wire 45 which reduces noise due to movement of the circuitry assembly 35 relative to the optical sensor 30. The alternating portions of the connection wire 45 absorb the shock of lateral movement and oscillating movement of the circuitry assembly 35 relative to the optical sensor 30.

The monitoring device 20 preferably has a short-range wireless transceiver 36*b* which is preferably a transmitter operating on a wireless protocol, e.g. BLUETOOTH, part-15, or 802.11. The short-range wireless transceiver preferably utilizes a conventional low-power, short-range wireless communication protocol, operating at a frequency such as 2.4 GHZ, 925 MHz, 433 MHz, or the like. The short-range wireless transmitter 36*b* (e.g., a BLUETOOTH transmitter) receives information from the microprocessor and transmits this information in the form of a packet through an antenna. A television, a computer or hand-held device features a similar antenna coupled to a matched wireless, short-range receiver that receives the information packet from the monitoring device 20. In certain embodiments, the hand-held device is a cellular telephone with a BLUETOOTH circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device is a pager or PDA.

Figure 5:
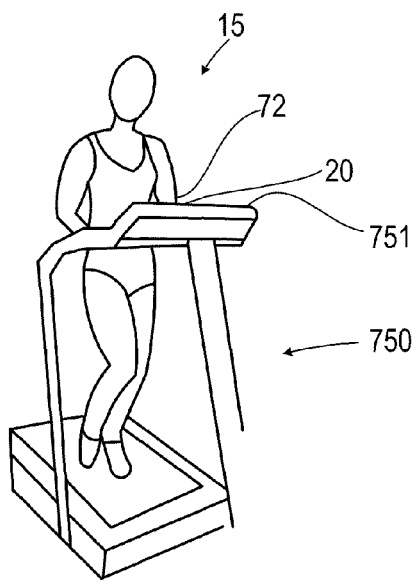
FIG. 5 is a front view of a user running on exercise equipment with the monitoring device on her arm.
Figure 6:
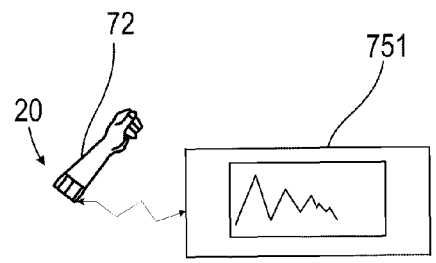
FIG. 6 is an isolated view of a display unit of the exercise equipment of FIG. 5.

As shown in FIGS. 5 and 6, in yet an alternative system utilizing the monitoring device 20, a user 15 wears the monitoring device 20 on the user's arm while exercising on exercise equipment 750. In this embodiment, a wireless signal is transmitted to the exercise equipment 750 to be displayed on a display 751 of the exercise equipment 750. In this embodiment, it is unnecessary for the monitoring device 20 to have a display 40 since the information is transmitted to the exercise equipment 750. As shown in FIG. 5, a user 15 preferably wears the monitoring device 20 on her arm 72 over the radial artery.

A general method is as follows. The light source 135 transmits light through at least one artery of the user. The photo-detector 130 detects the light. The pulse rate is determined by the signals received by the photo-detector 130. An optical sensor 30 with a photodetector 130 and LEDs 135 are preferably utilized.

This information is sent to the circuitry assembly 35 for creation of user's real-time pulse rate. The microprocessor 41 further processes the information to display pulse rate, calories expended by the user of a pre-set time period, target zones of activity, time and/or dynamic blood pressure. The information is displayed on a display member or electro-optical display.

In an alternative embodiment, the housing 95 has three control buttons 43*a-c*. The control buttons 43*a-c* are preferably positioned in relation to the display member 40 to allow the user immediate visual feedback of the user's inputted information. The middle control button 43*b* preferably activates and deactivates the article 25. The left button 43*a* is preferably used to scroll through the different modes. The right button 43*c* is preferably used to input data. The control buttons 43*a-c* allow for the user's personal data to be entered and for choices to be selected by the user. The left button 43*a* preferably allows for the user's calories burned to be displayed on the display member 40 and for the activity to be reset, and allows for other fitness monitoring features to be displayed.

To activate the article 25, the middle button 43*b* is depressed for preferably 0.5 seconds and then released. The display member will appear with a current pulse of the user and a calories burned display. The microprocessor preferably stores the calories burned and accumulates the values for a daily calories burned value and a total calories burned value until the activity is reset.

To enter the user's personal data, the middle button 43*b* is depressed for 2 seconds and then released. The user will enter gender, age, mass, height and resting heart rate. Entering the data entails pushing the middle button to select a category (gender, age, . . . ) and then pushing the right or left button to scroll through the available options or to enter a value (e.g. age of the user). The middle button 43*b* is pressed again to save the entry. This process is preformed until the user's has entered all of the data that the user wishes to enter into the microprocessor. The display member 40 will then display a heart rate and current calories burned value. A preset resting heart rate for men and women is preferably stored on the microprocessor, and used as a default resting heart rate. However, the user may enter his/her own resting heart rate value if the user is aware of that value. To access daily calories, the left button 43*a* is pushed by the user and the display member 40 will illustrate the value for daily calories burned by the user.

If the left button 43*a* is pushed again, the value for total calories burned by the user will be displayed on the display member 40. The left button 43*a* is pushed again to return to a heart rate value on the display member 40.

The right button 43*c* is pushed to scroll through the choices of other output values, which comprises: basal metabolic rate; average heart rate; minimum heart rate; maximum heart rate; fat burn heart rate exercise target zone; cardio burn heart rate exercise target zone; and, summary of daily calories burned. The basal metabolic rate (displayed as "BMR") is an estimate of the total calories burned by the user in one day without exercise, and is based on the user inputted personal data. The average heart rate (displayed as "avHR") is the average heart rate of the user between resets, and is an overall indicator of fitness. The lower the average heart rate, the healthier the heart. The average heart rate is also a measure of the effectiveness of the exercise program employed by the user since a decrease in the average heart rate of the user will indicate the user's fitness has improved. The minimum heart rate (displayed as "mnHR") of the user is typically measured during sleep and periods of relaxation. The maximum heart rate (displayed as "mxHR") is typically measured during intense workouts. The fat burn heart rate exercise target zone (displayed as "fatB") displays a low and high range for the heart rate of the user to optimize fat burning during exercise. The cardio burn heart rate exercise target zone provides a high and low range for the heart rate of the user to optimize cardio conditioning during exercise. The summary of daily calories burned (displayed as "cal") displays the daily calories burned by the user.

In a preferred embodiment, an accelerometer is embedded within the article 25 and connected to the circuitry assembly 35 in order to provide information on the distance traveled by the user. In a preferred embodiment, the accelerometer is a multiple-axis accelerometer, such as the ADXL202 made by Analog Devices of Norwood, Mass. This device is a standard micro-electronic-machine ("MEMs") module that measures acceleration and deceleration using an array of silicon-based structures.

In yet another embodiment, the monitoring device 20 comprises a first thermistor, not shown, for measuring the temperature of the user's skin and a second thermistor, not shown, for measuring the temperature of the air. The temperature readings are displayed on the display member 40 and the skin temperature is preferably utilized in further determining the calories expended by the user during a set time period. One such commercially available thermistor is sold under the brand LM34 from National Semiconductor of Santa Clara, Calif. A microcontroller that is utilized with the thermistor is sold under the brand name ATMega 8535 by Atmel of San Jose, Calif.

The monitoring device 20 is able to download the information to a computer for further processing and storage of information. The download may be wireless or through cable connection. The information can generate an activity log or a calorie chart.

The microprocessor can use various methods to calculate calories burned by a user. One such method uses the Harris-Benedict formula. Other methods are set forth at unu.edu/unupress/food2, which relevant parts are hereby incorporated by reference. The Harris-Benedict formula uses the factors of height, weight, age, and sex to determine basal metabolic rate (BMR). This equation is very accurate in all but the extremely muscular (will underestimate calorie needs) and the extremely overweight (will overestimate caloric needs) user.

The equations for men and women are set forth below:

Men: BMR=66+(13.7×mass(kg))+(5×height(cm))−(6.8×age(years))

Women: BMR=655+(9.6×mass)+(1.8×height)−(4.7×age)

The calories burned are calculated by multiplying the BMR by the following appropriate activity factor: sedentary; lightly active; moderately active; very active; and extra active.

Sedentary=BMR multiplied by 1.2(little or no exercise, desk job)

Lightly active=BMR multiplied by 1.375(light exercise/sports 1-3 days/wk)

Moderately Active=BMR multiplied by 1.55(moderate exercise/sports 3-5 days/wk)

Very active=BMR multiplied by 1.725(hard exercise/sports 6-7 days/wk)

Extra Active=BMR multiplied by 1.9(hard daily exercise/sports & physical job or 2×day training, marathon, football camp, contest, etc.)

Various target zones may also be calculated by the microprocessor. These target zones include: fat burn zone; cardio zone; moderate activity zone; weight management zone; aerobic zone; anaerobic threshold zone; and red-line zone.

Fat Burn Zone=(220−age)×60% & 70%

An example for a thirty-eight year old female:
i. (220−38)×0.6=109
ii. (220−38)×0.7=127
iii. Fat Burn Zone between 109 to 127 heart beats per minute.

Cardio Zone=(220−your age)×70% & 80%

An example for a thirty-eight year old female:
i. (220−38)×0.7=127
ii. (220−38)×0.8=146
iii. Cardio zone is between 127 & 146 heart beats per minute.

Moderate Activity Zone, at 50 to 60 percent of your maximum heart rate, burns fat more readily than carbohydrates. That is the zone one should exercise at if one wants slow, even conditioning with little pain or strain.

Weight Management Zone, at 60 to 70 percent of maximum, strengthens ones heart and burns sufficient calories to lower one's body weight.

Aerobic Zone, at 70 to 80 percent of maximum, not only strengthens one's heart but also trains one's body to process oxygen more efficiently, improving endurance.

Anaerobic Threshold Zone, at 80 to 90 percent of maximum, improves one's ability to rid one's body of the lactic-acid buildup that leads to muscles ache near one's performance limit. Over time, training in this zone will raise one's limit.

Red-Line Zone, at 90 to 100 percent of maximum, is where serious athletes train when they are striving for speed instead of endurance.

Example One

Female, 30 yrs old, height 167.6 centimeters, weight 54.5 kilograms.

The BMR=655+523+302−141=1339 calories/day.

The BMR is 1339 calories per day. The activity level is moderately active (work out 3-4 times per week). The activity factor is 1.55. The TDEE=1.55×1339=2075 calories/day. TDEE is calculated by multiplying the BMR of the user by the activity multiplier of the user.

The heart rate may be used to dynamically determine an activity level and periodically recalculate the calories burned based upon that factor. An example of such an activity level look up table might be as follows:

Activity/Intensity Multiplier Based on Heart Rate

Sedentary=BMR×1.2(little or no exercise, average heart rate 65-75 bpm or lower)

Lightly active=BMR×3.5(light exercise, 75 bpm-115 bpm)

Mod. active=BMR×5.75(moderate exercise, 115-140 pm)

Very active=BMR×9.25(hard exercise, 140-175 bpm)

Extra active=BMR×13(175 bpm-maximum heart rate as calculated with MHR formula)

For example, while sitting at a desk, a man in the above example might have a heart rate of between 65 and 75 beats per minute (BPM). (The average heart rate for an adult is between 65 and 75 beats per minute.) Based on this dynamically updated heart rate his activity level might be considered sedentary. If the heart rate remained in this range for 30 minutes, based on the Harris-Benedict formula he would have expended 1.34 calories a minute×1.2 (activity level)×30 minutes, which is equal to 48.24 calories burned.

If the man were to run a mile for 30 minutes, with a heart rate ranging between 120 and 130 bpm, his activity level might be considered very active. His caloric expenditure would be 1.34 calories a minute×9.25 (activity level)×30 minutes, which is equal to 371.85.

Another equation is weight multiplied by time multiplied by an activity factor multiplied by 0.000119.

Figure 7:
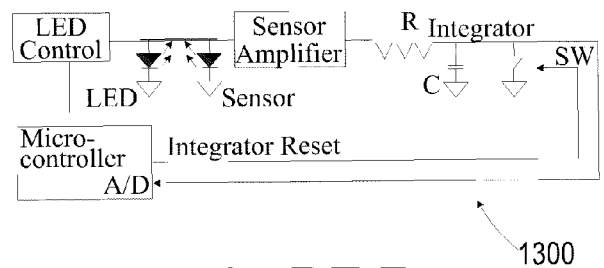
FIG. 7 is a schematic flow chart of the signal acquisition step of the flow chart of FIG. 10.
Figure 11:
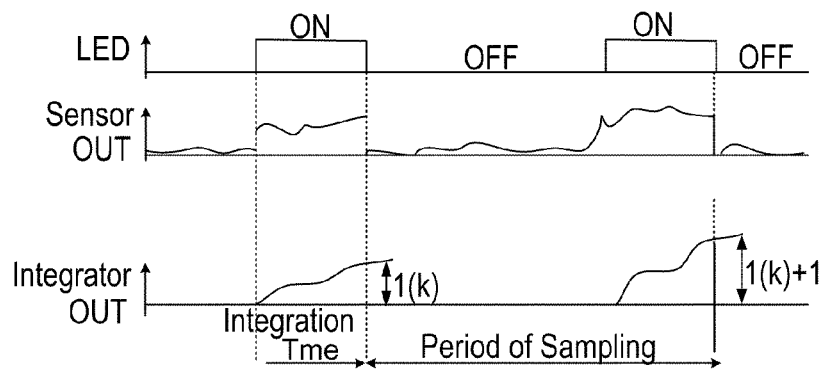
FIG. 11 is an illustration of the waveforms of the data sampling during the signal processing method.
Figure 10:
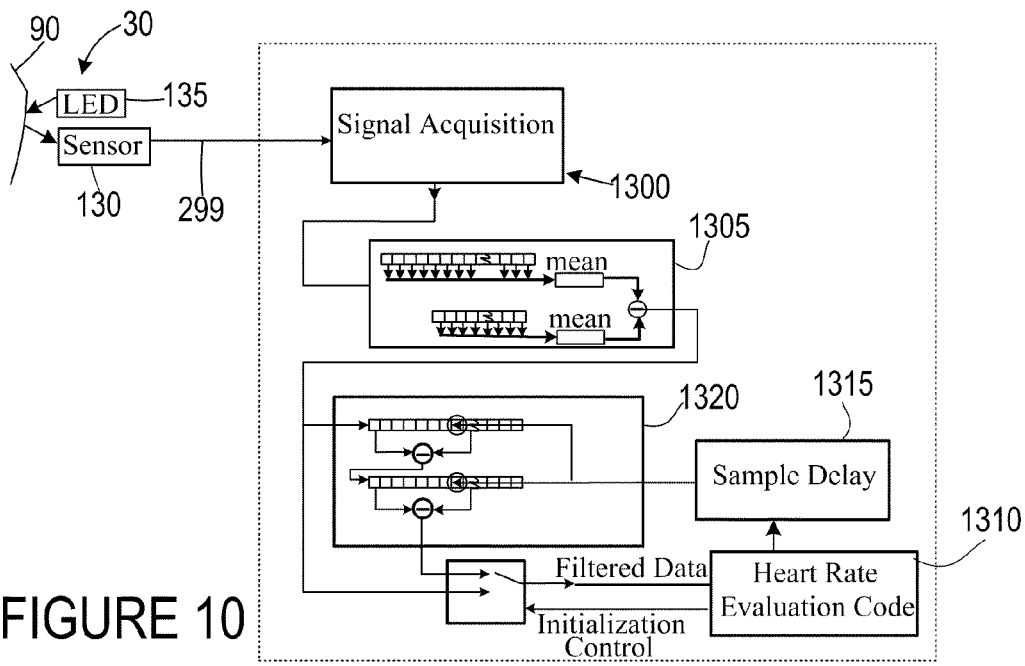
FIG. 10 is a flow chart of a signal processing method of the present invention.

FIG. 10 illustrates a block diagram of a flow chart of a signal processing method of the present invention. As shown in FIG. 10, the photodetector 130 of the optical sensor 30 receives light from the light source 135 while in proximity to the user's artery. The light source 135 is preferably a plurality of LEDs 135. In a preferred embodiment, the optical sensor 30 is a TRS1755 which includes a green LED light source (567 nm wavelength) and a light-to-voltage converter. The output voltage is directly proportional to the reflected light intensity. The signal 299 is sent to the microprocessor 41. At block 1300, the signal acquisition is performed. As shown in FIG. 7, in the pulse mode the LED 135 is periodically activated for short intervals of time by a signal from the microcontroller. The reflected pulse of light is received by the sensor, with the generation of a voltage pulse having an amplitude proportional to the intensity of the reflected light. When the LED is activated, the switch, SW, is open by the action of the control signal from the microcontroller, and the capacitor, C, integrates the pulse generated from the sensor by charging through the resistor R. Immediately prior to deactivation of the LED, the analog-to-digital converter acquires the value of the voltage integrated across the capacitor, C. The analog-to-digital converter generates a data sample in digital form which is utilized by the microcontroller for evaluation of the heart rate the wearer. Subsequent to the sample being acquired by the analog-to-digital converter, the LED is deactivated and the capacitor, C, is shortcut by switch, SW, to reset the integrator, RC. A signal indicating sensor saturation is also sent to the microcontroller for light control of the LEDs. This states remains unchanged for a given time interval after which the process is repeated, which is illustrated in FIG. 11. The signals are shown in FIG. 11, with the raw sensor signal received from the sensor amplifier shown as varying between reflected light when the LEDs are on and an ambient light level when the LEDs are off. The filtered signal from the high pass filter ("HPF") is shown as the filtered sensor signal in FIG. 7. The integrator reset signal is shown as integrator out signal in FIG. 11, and the integrator reset signal in FIG. 7. A noise reduction and power reduction process is discussed below in reference to FIGS. 13 and 14.

At block 1305, a band pass filter is implemented preferably with two sets of data from the analog-to-digital converter. At block 1305, an average of the values of data samples within each of a first set of samples is calculated by the microprocessor. For example, the values of data samples within forty-four samples are summed and then divided by forty-four to generate an average value for the first set of samples. Next, an average of the values of data samples within a second set of samples is calculated by the microprocessor. For example, the values of data samples within twenty-two samples are summed and then divided by twenty-two to generate an average value for the second set of samples. Preferably, the second set of samples is less than the first set of samples. Next, the average value of the second set of samples is subtracted from the average value for the first set of samples to generate a first filtered pulse data value.

At block 1310, the filtered pulse data value is processed using a heart rate evaluation code to generate a first heart rate value. In a preferred method, the heart rate evaluation code obtains the heart rate by calculating the distance between crossing points of the voltage through zero. Once the first heart rate value is known, then an adaptive resonant filter is utilized to generate a filtered second heart rate value by attenuating interference caused by motion artifacts. At block 1315, a sample delay is computed as the period of evaluated heart rate divided by two.

At block 1320, preferably a two cascade adaptive resonant filter generates a second filtered pulse data value which is processed at block 1310 using the heart rate evaluation code to generate a second heart rate value. Those skilled in the pertinent art will recognize that three, four, or more, cascade adaptive resonant filters may be utilized in generating the second filtered pulse data value. Essentially, the highest and lowest values are disregarded in calculating the filtered second heart rate value. Alternatively, a phase is established and any values outside of the phase are disregarded in calculating the second heart rate value. The filtering is preferably continued during the use of the monitor thereby further refining the heart rate value of the user.

Figure 12:
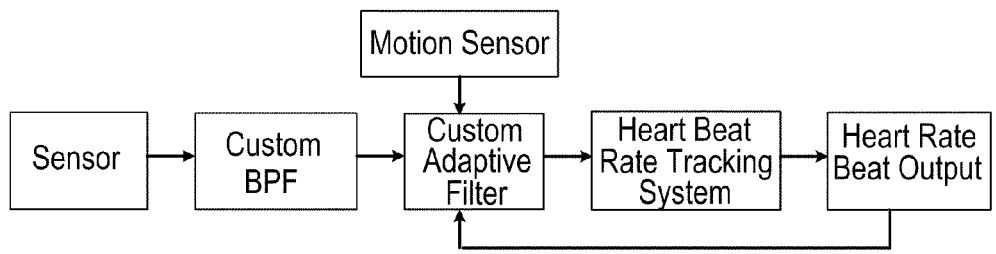
FIG. 12 is a flow chart of a portion of the signal processing step utilizing a motion sensor to reduce the affect of motion.

As shown in FIG. 12, a motion sensor 1100 is included in a preferred embodiment to assist in identifying motion noise and filtering the noise from the signal sent by the sensor 30. The motion sensor 1100, such as an accelerometer, is integrated into the circuitry and software of the monitoring device 20. As the motion sensor detects an arm swinging, the noise component is utilized with the signal processing noise filtering techniques to provide additional filtering to remove the noise element and improve the accuracy of the monitoring device 20. More specifically, the signal from the sensor 30 is transmitted to the processor where a custom blood pressure filter 41$w$ processes the signal which is further processed at by custom adaptive filter 41$x$ before being sent to a heart beat tracking system 41$y$ and then transmitted to a heart rate beat output 41z. The heart rate beat output 41z provides feedback to the custom adaptive filter 41x which also receives input from the motion sensor 1100.

Still further, a battery source containing twin AAA batteries is built into a buckle for the straps 26a and 26b. The battery holder is preferably similar in appearance to a shoe buckle.

Figure 13:
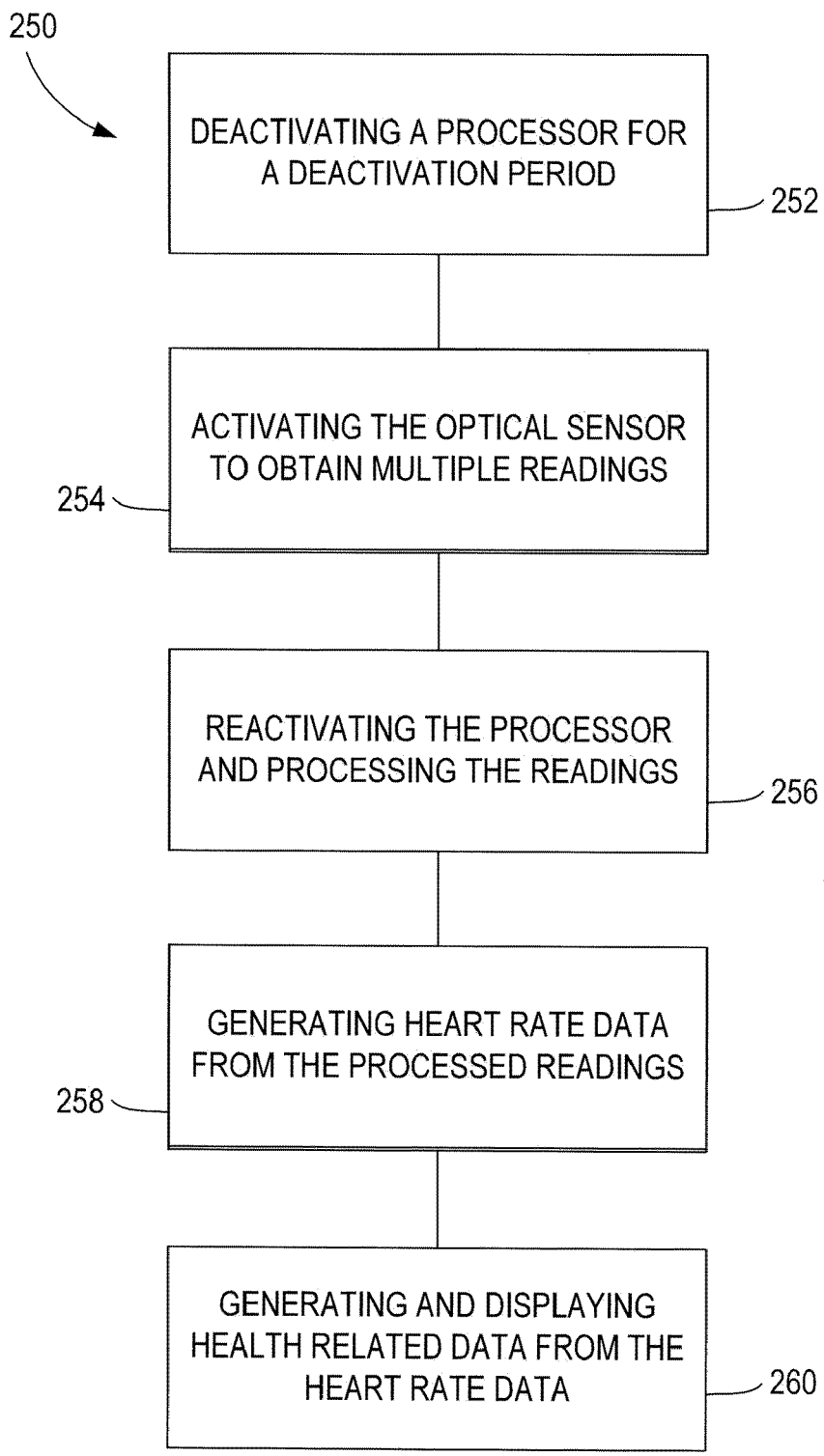
FIG. 13 is a flow chart of a noise reduction method of the present invention.

FIG. 13 illustrates a noise reduction method of the present invention. Due to the desire to minimize power consumption of the monitoring device 20, and achieve very accurate signal measurements using the optical sensor 30, the present invention preferably utilizes the method 200 illustrated in FIG. 13. At block 202, the processor 41 is deactivated for a deactivation period in order to conserve power and to eliminate noise for a signal measurement. The deactivation period ranges from 128 to 640 microseconds, more preferably from 200 microseconds to 400 microseconds, and more preferably from 225 microseconds to 300 microseconds. In reference to FIG. 10, this deactivation period occurs during block 1300. At block 204, during the deactivation period, the optical sensor 30 is activated to obtain multiple readings using the light source 135 and the photodetector 130. Preferably 4 to 25 sub-readings or sub-samples are obtained during the deactivation period. The sub-readings or sub-samples are averaged for noise reduction to provide a reading or sample value. In a single second, from 500 to 1500 sub-readings or sub-samples are obtained by the optical sensor 30. At block 206, the processor 41 is reactivated and the reading values are processed by processor 41. At block 208, heart rate data is generated from the readings by the processor 41. At block 210, health related data is generated from the heart rate data, and the health related data and the heart rate data are displayed on the display member 40.

Figure 14:
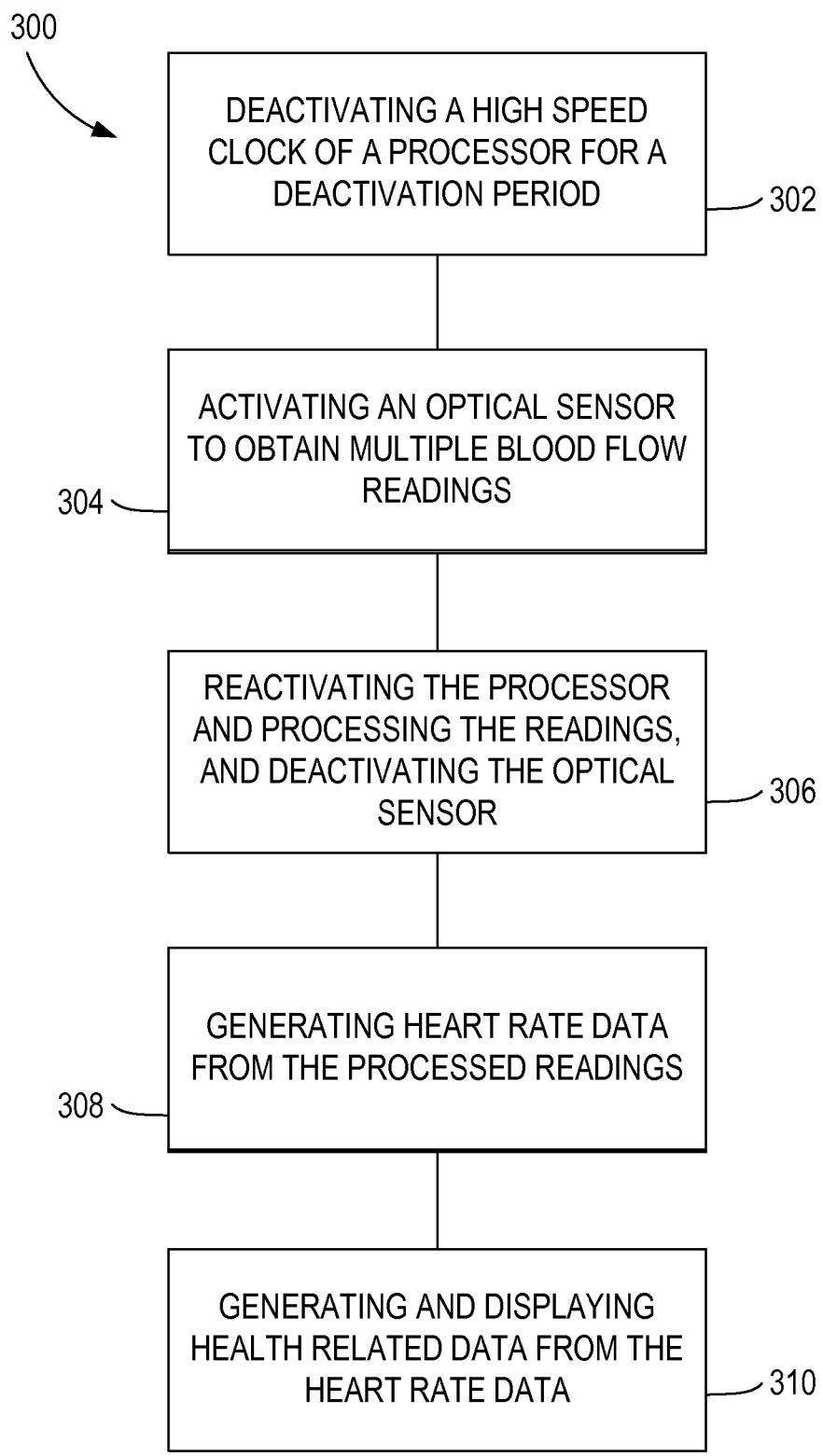
FIG. 14 is a flow chart of a specific noise reduction method of the present invention.

FIG. 14 illustrates a more specific method 300 for noise reduction during a signal reading. At block 302, a high speed clock of a processor 41 is deactivated for a deactivation period as discussed above. At block 304, the optical sensor 30 is activated during the deactivation period to obtain multiple readings as discussed above. At block 306, the processor 41 is reactivated and the readings are processed. The optical sensor 30 is also deactivated. At block 308, heart rate data is generated from the readings by the processor 41. At block 310, health related data is generated from the heart rate data, and the health related data and the heart rate data are displayed on the display member 40.

Figure 17:
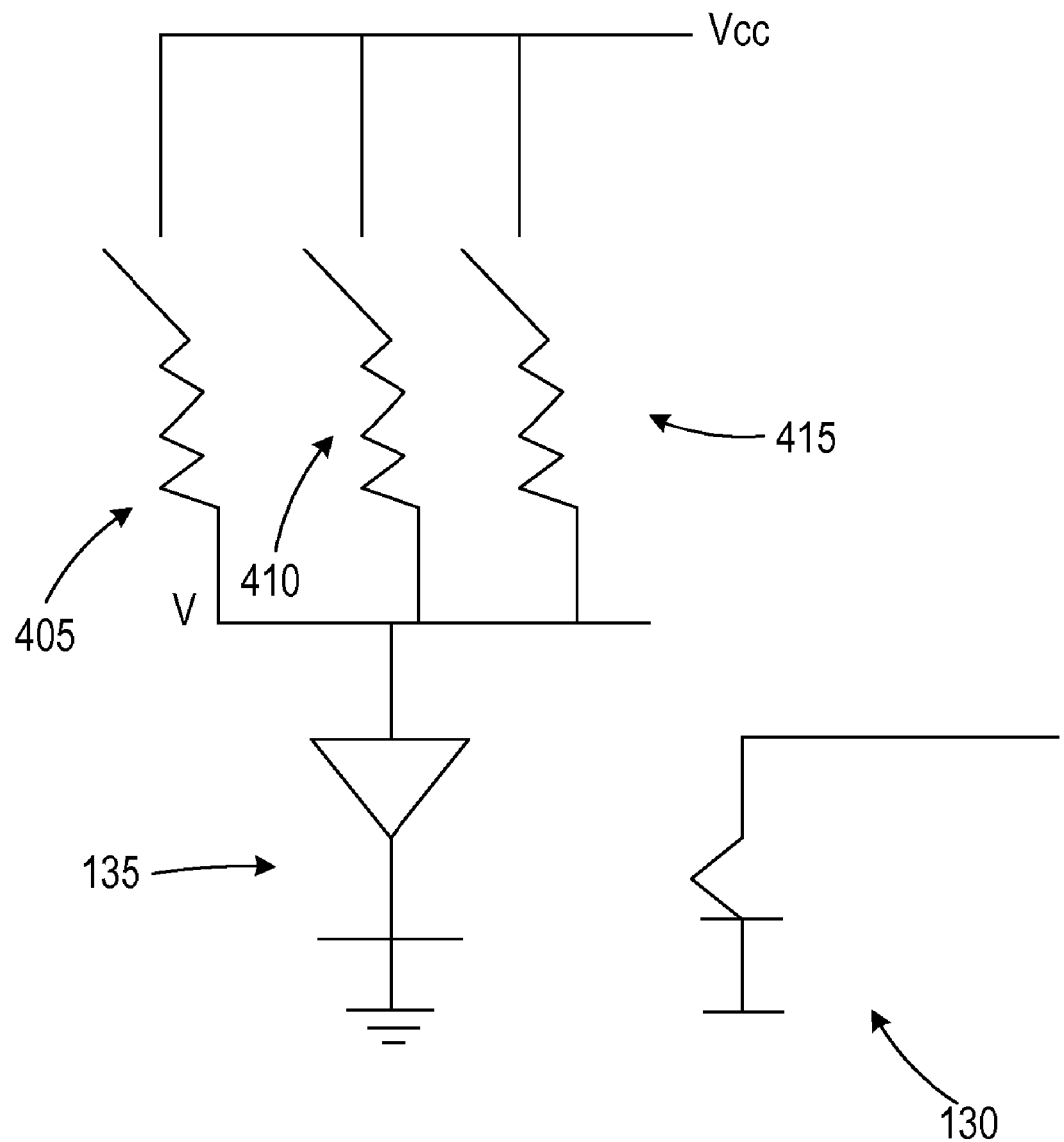
FIG. 17 is a schematic diagram of a light source intensity controlling mechanism of the present invention.

FIG. 17 illustrates a mechanism for controlling the intensity of the light source 135 using a plurality of resistors 405, 410 and 415 in parallel. Usually, an optical sensor 30 has a light source 135 set for a single intensity for placement at a single location on a user. However, if the optical sensor 30 is placed at a different location, e.g. from the lower arm to the upper arm, the intensity of the light source 135 may be too great for the photodetector 130 and lead to saturation of the photodetector 130 which terminates the signal reading. The present invention preferably adjusts the intensity of the light source 135 using feedback from the photodetector 130 to indicate whether the light intensity is too high or too low. As shown in FIGS. 17, 17A, 17B and 17C, the current flow through the resistors 405, 410 and 415 is changed, which results in changes in the light intensity of the light source 135. Equation A below illustrates the resistance:

$$1/R_{\mathit{eff}} = S_1(1/R_1) + S_2(1/R_2) + S_3(1/R_3)$$

where $S_n$=Switch$_n$ having a value of 0 or 1, and $R_n$=resistor, in ohms. In one embodiment, resistor 405 has a resistance of 400 Ohms, resistor 410 has a resistance of 200 Ohms and resistor 415 has a resistance of 100 Ohms. Various combinations of the resistors can be switched on to control the light intensity.

Figure 17A:
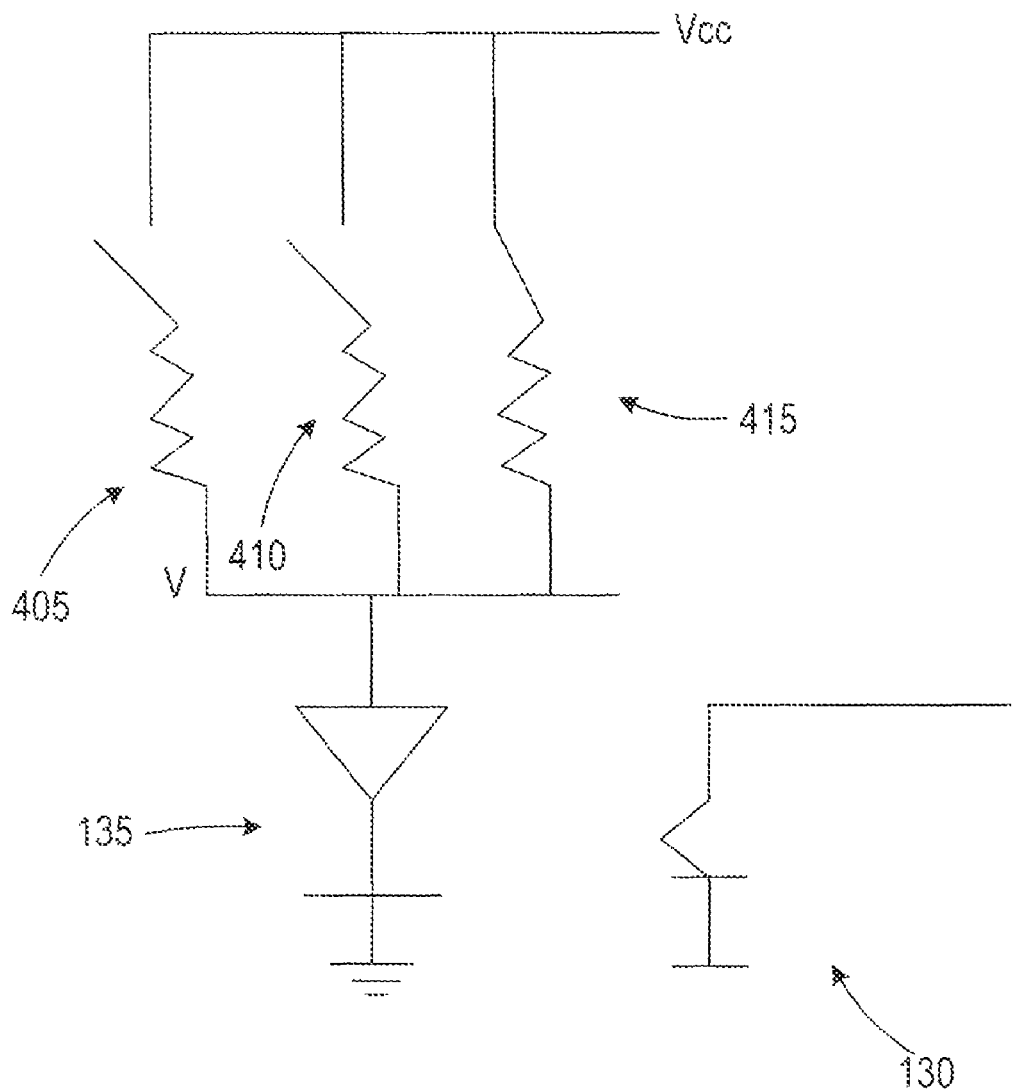
FIG. 17A is a schematic diagram of the light source intensity controlling mechanism of FIG. 17 with a single resistor connected.
Figure 17B:
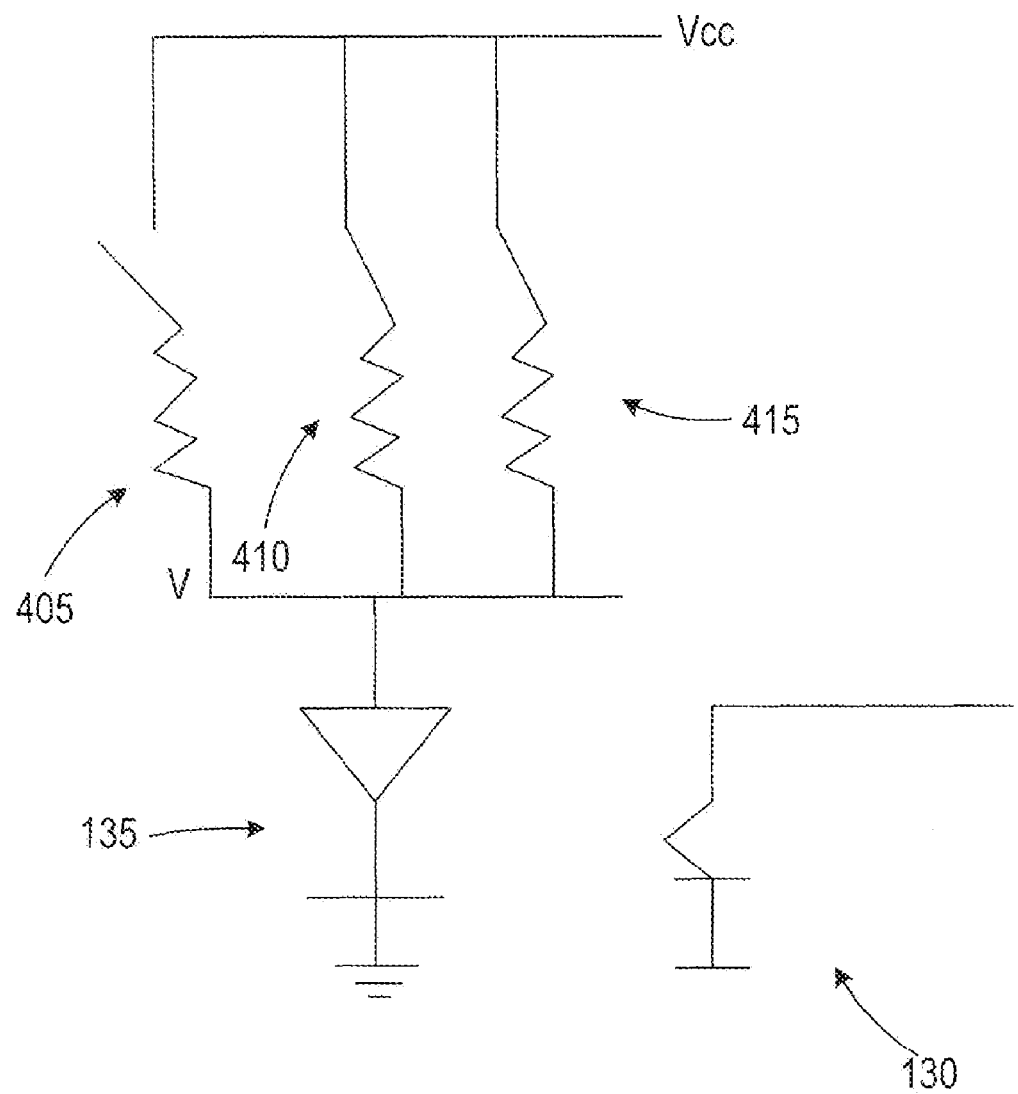
FIG. 17B is a schematic diagram of the light source intensity controlling mechanism of FIG. 17 with a single resistor connected.
Figure 17C:
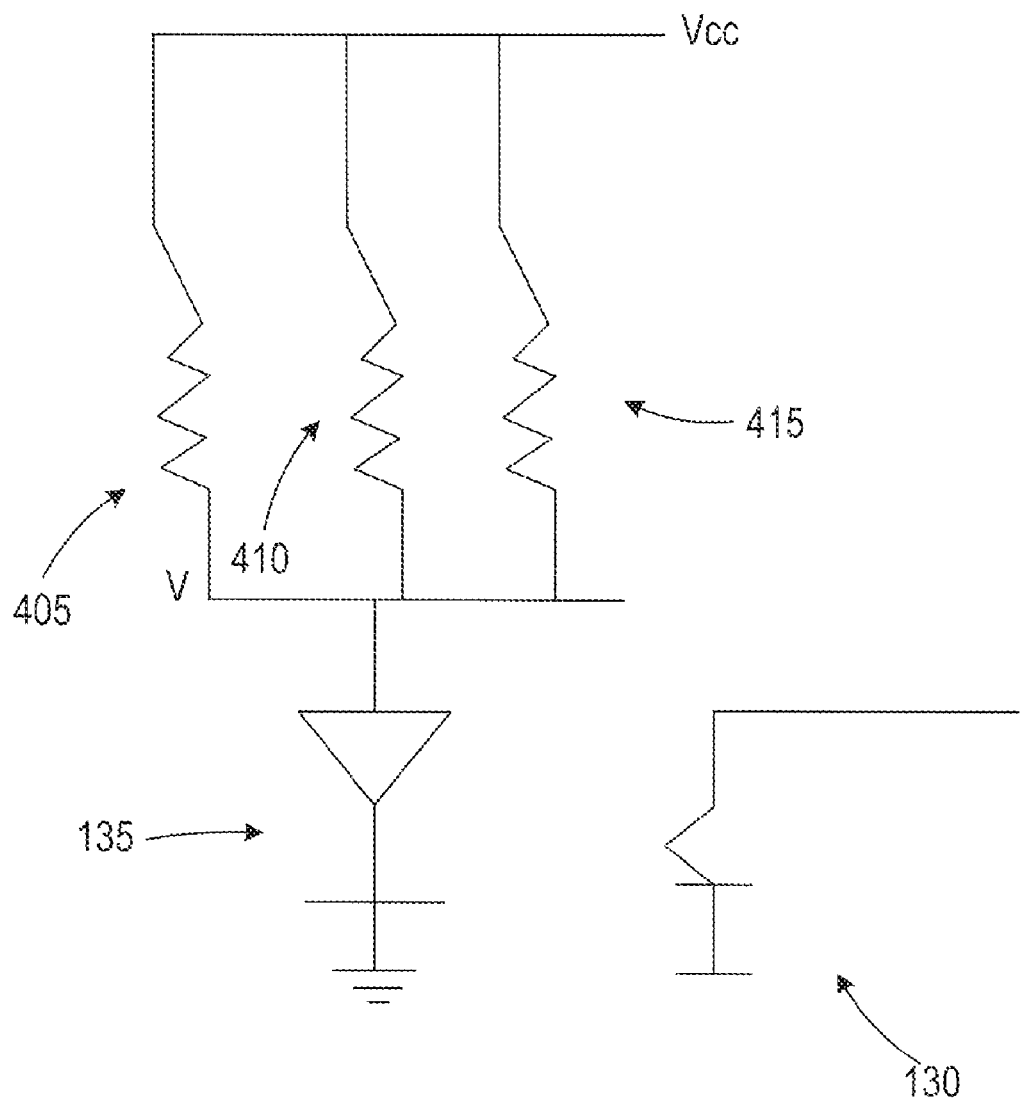
FIG. 17C is a schematic diagram of the light source intensity controlling mechanism of FIG. 17 with two resistors connected.

FIG. 17A has current flowing through a single line and a single resistor. FIG. 17C has current flowing through all of the lines. Although FIG. 17C utilizes the most resistors 410 and 415, it has the greatest current flow and the highest intensity. The current flow is given by the equation B:

$$(V_{cc} - V)/R_{\mathit{eff}} = I_{LED}$$

where $I_{LED}$ is the current flow. Although only three resistors are shown, those skilled in the pertinent art will recognize the more or fewer resistors may be used without departing from the scope and spirit of the present invention.

Figure 18:
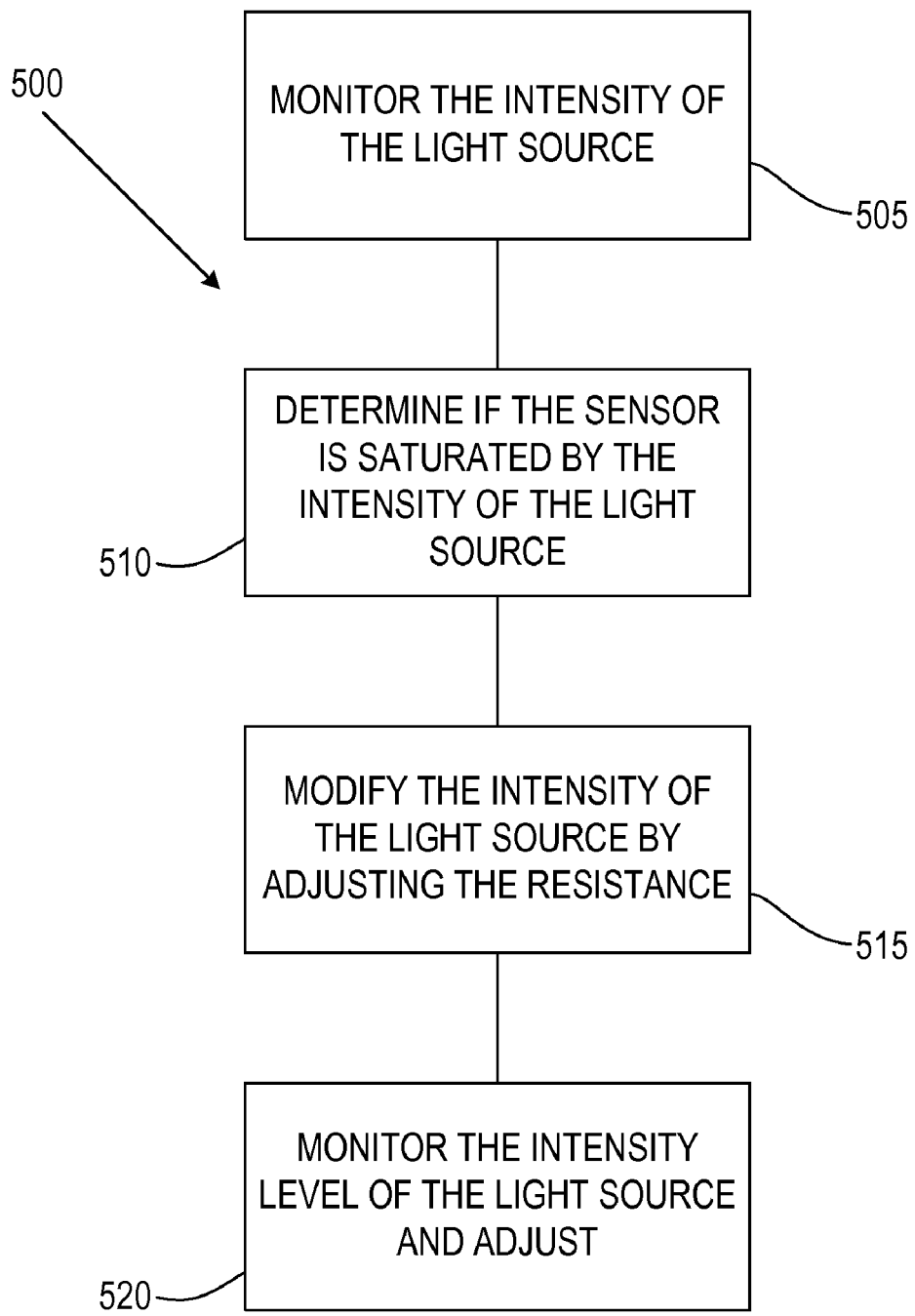
FIG. 18 is a flow chart of a light source intensity controlling method of the present invention.

FIG. 18 is a preferred method 500 for controlling the light intensity of the optical sensor 30. At block 505, the light intensity of the light source 135 is monitored. At block 510, the sensor/photodetector is determined to be saturated by the light source. At block 515, the intensity of the light source is modified by adjusting the resistance and the flow of current to the light source 135. At block 520, the light intensity is again monitored and adjusted if necessary. In a preferred embodiment, this automatic gain mechanism prevents the green light from overwhelming the photodetector thereby maintaining an accurate reading no matter where the optical sensor is placed on the user.

Figure 19:
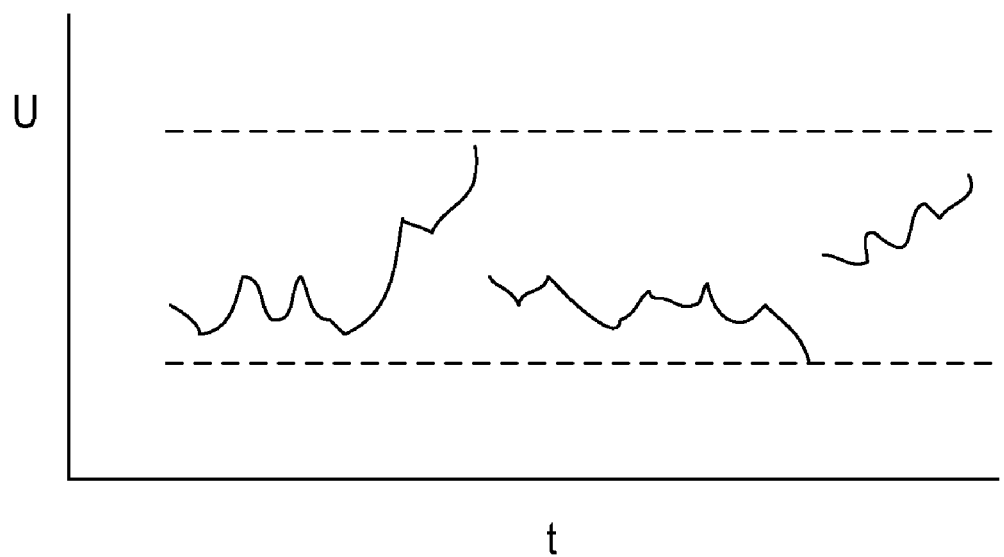
FIG. 19 is a graph illustrating the method and mechanism of controlling the intensity of the light source over time.

FIG. 19 illustrates how the control mechanism operates to maintain a proper light intensity. As the signal reaches the upper limit, the photodetector becomes saturated and the processor lowers the current flow, which results in a break in the signal. Then as the signal is lowered it becomes too low and the processor increases the light intensity resulting in a break in the signal.

Figure 20:
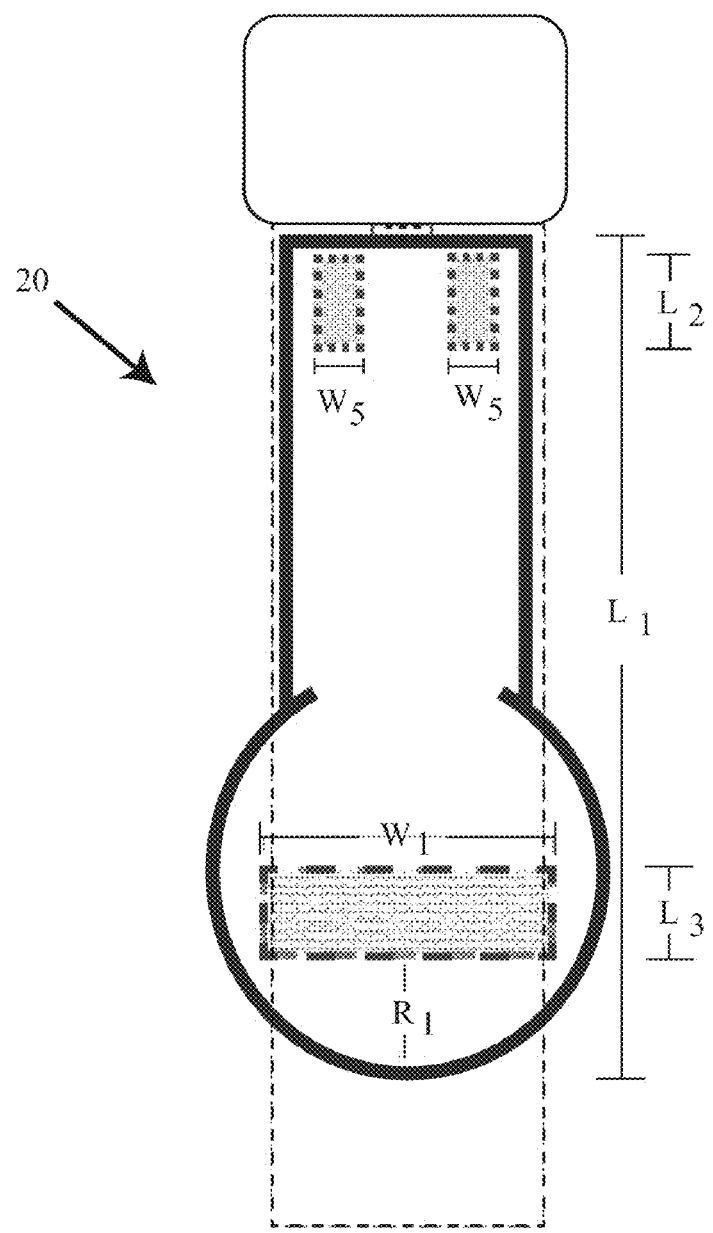
FIG. 20 is a plan view of a monitoring device.
Figure 20A:
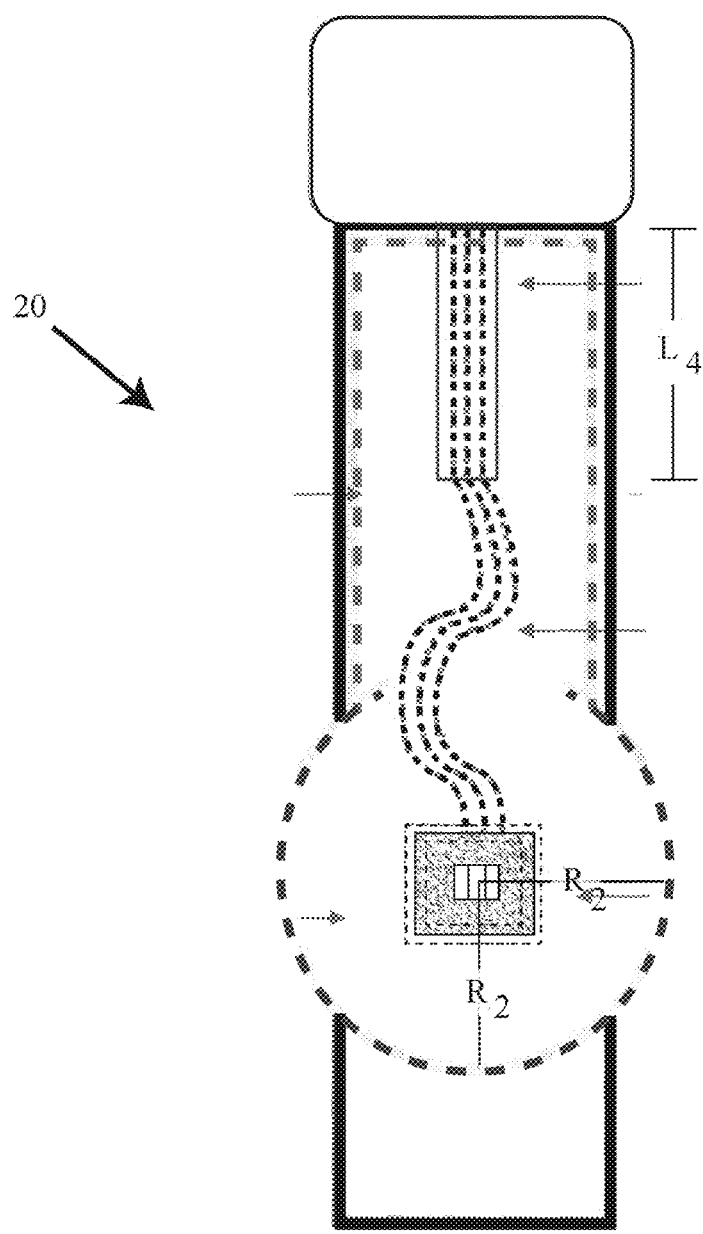
FIG. 20A is a plan view of an opposite side of the monitoring device of FIG. 20.
Figure 20B:
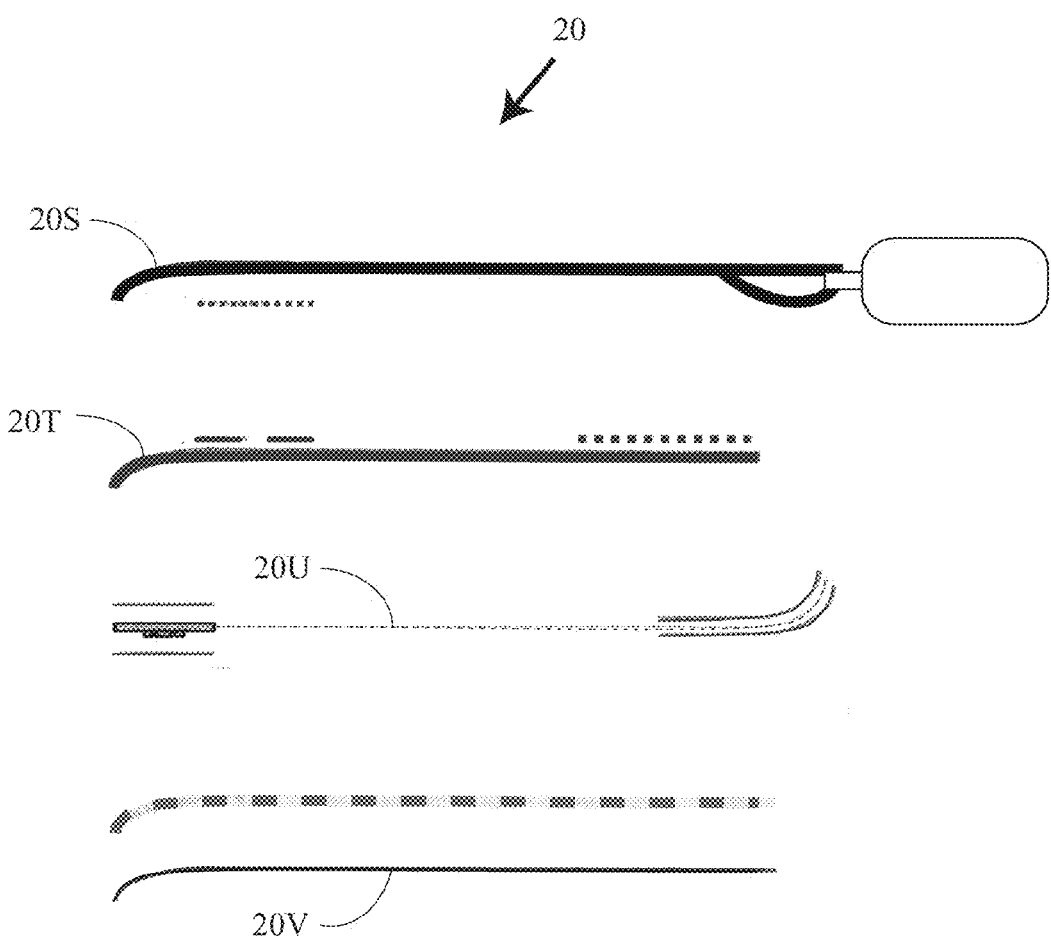
FIG. 20B is an exploded view of the monitoring device of FIG. 20.

As shown in FIGS. 20, 20A and 20B, a monitoring device 20 is composed of several components including an armband 20S with a VELCRO loop, a sensor flap back 20T with a VELCRO hook and an elastic armband mount, a sensor board 20U with wiring, and non-allergic cotton liner 20V. FIG. 20 illustrates the monitoring device 20 with elastic material having a width W1 ranging from 1.5 inches to 1.75 inches, and widths W5 ranging from 0.25 inch to 0.5 inch. The length L1 is preferably 3 to 4 inches in length, the lengths L2 and L3 are preferably 0.5 to 0.75 inch in length. As shown in FIG. 20A, the monitoring device 20 has a sensor mounted a distance of R2 from the edge, wherein R2 ranges from 1 inch to 1.25 inches. The cotton sensor mount liner and sweat channeling material are assembled by double sided adhesive material on back of cotton liner, with the sweat channeling material visible through the larger hole in the cotton material after assembly using the double sided adhesive. Double sided adhesive is preferably used to place small sweat channeling patch (1¼" by 1") on back of sensor board. The Neoprene sensor pad, loop VELCRO, and elastic armband mounts are sewn on the sensor flap back. The loop VELCRO material attaches to the hook VELCRO material mounted on sensor strap. The sensor mount with double sided adhesive is applied on the bottom. No adhesive is on the lower half to allow the wires to float. The sensor is lined up with small hole and attached with double sided adhesive material. No material or thread should touch the sensor or LEDs. The neoprene sensor pad is applied to the sensor mount assembly with the sweat channeling material and the loop VELCRO material facing outwards. The sensor pad is sewn preferably using black thread. Do not sew the bottom where the wires come out. Sew bias edging is preferred with blue thread around entire sensor assembly and no wires are sewn through.

Figure 21:
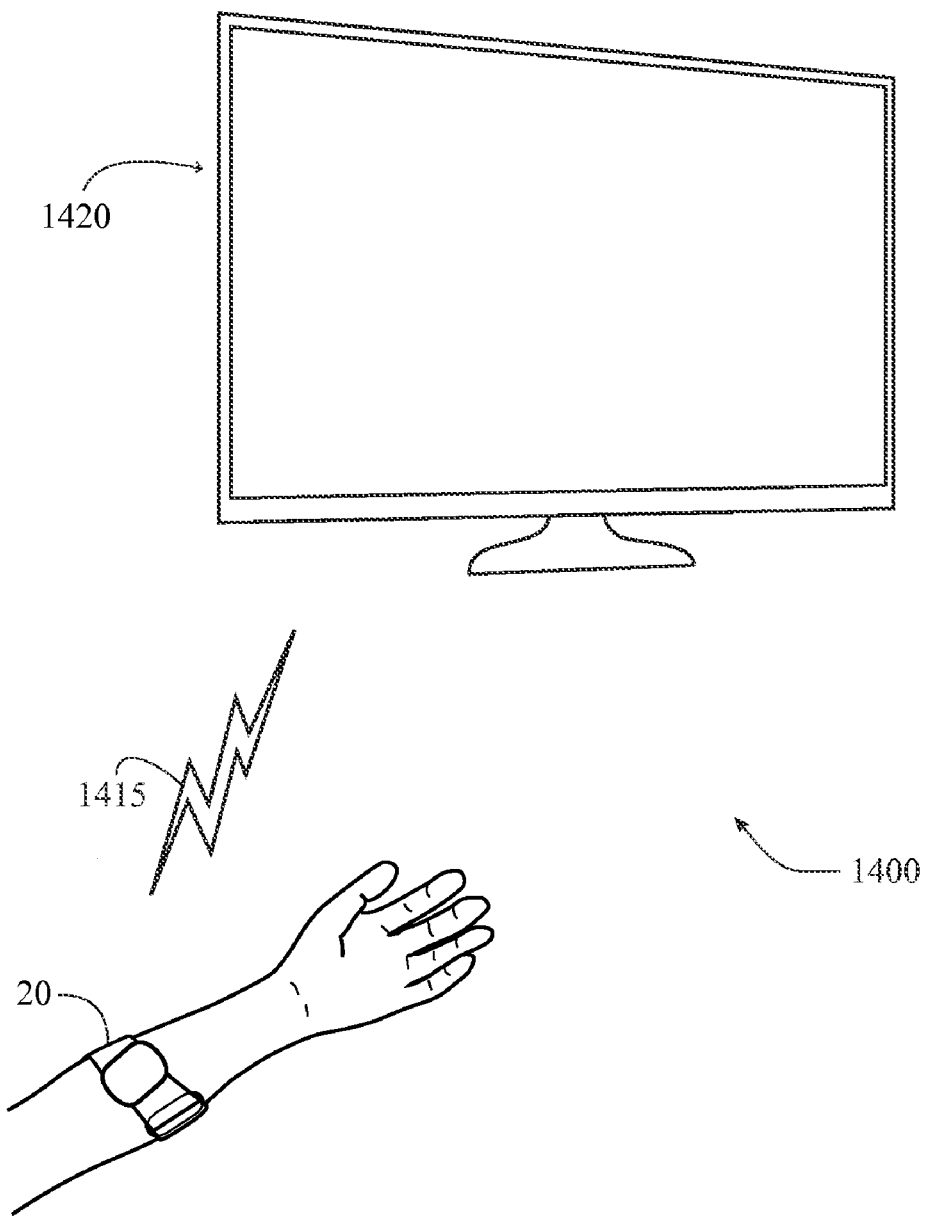
FIG. 21 a block diagram of an interactive game system with a player utilizing a monitoring device to play an interactive video game shown on a computer display screen.

As shown in FIG. 21 a system 1400 for an interactive game with a real-time vital sign monitoring device comprises a monitoring device 20 and a computer 1420. The monitoring device 20 is worn by a player of an interactive game which is displayed on a display screen 1425 of the computer 1420. A wireless signal 1415 is transmitted from the monitoring device to the computer 1420 while the player is playing the interactive game. The wireless signal includes real-time vital sign information about the user to be used in playing the interactive game.

Figure 22:
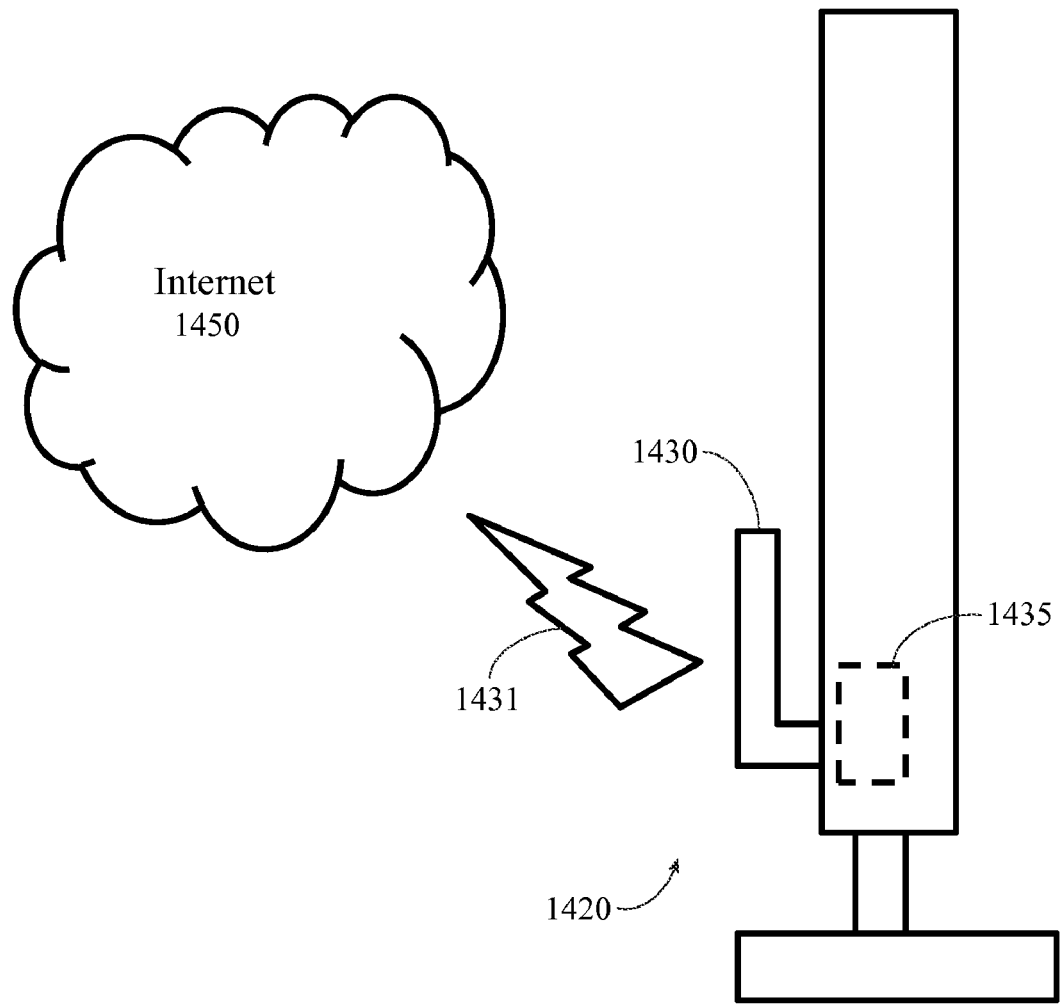
FIG. 22 is a side view of a computer along with a wireless communication to a network.

As shown in FIG. 22, the computer 1420 includes a wireless transceiver 1430 for receiving the signal from the monitoring device 20 and for wireless communicating with a network such as the Internet 1450 through wireless signal 1431. The computer 1420 also includes a processor 1435 for processing the data from the Internet 1450 or from the monitoring device 20.

Figure 23:
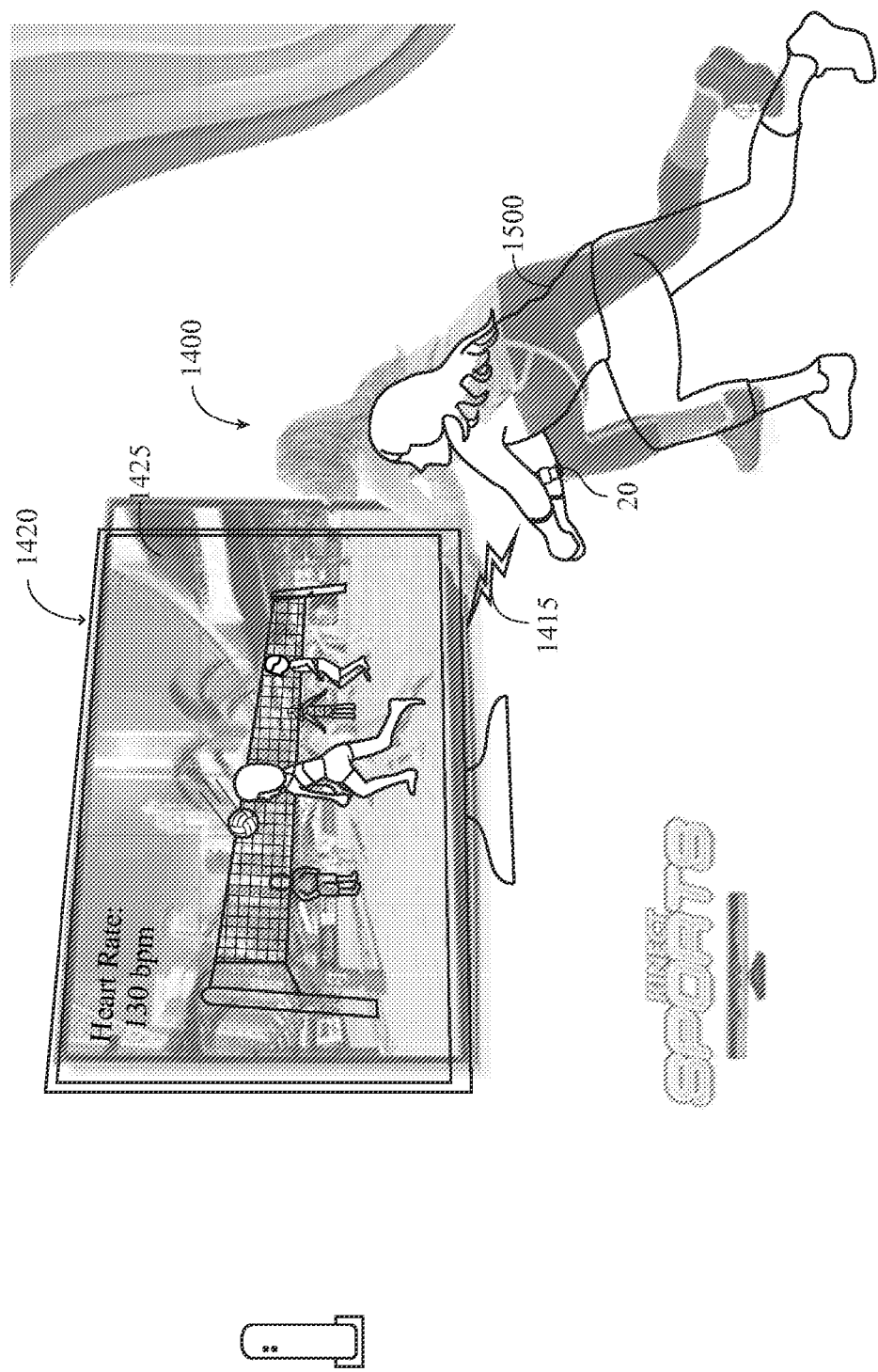
FIG. 23 a block diagram of a user utilizing a monitoring device to play an online interactive video game shown on a computer display screen.

As shown in FIG. 23, the system 1400 for an interactive game with a real time monitoring device comprises a monitoring device 20 with a wireless feature, and a computer 1420. The monitoring device 20 is worn on the player's arm and transmits a signal 1415 to the computer 1420. As a player 1500 performs actions representative of playing volleyball, a representation of the user on the display screen 1425 of the computer 1420 also performs the actions in an online volleyball game with other characters. The real-time heart rate of the user can also be shown on the display screen 1425.

The computer 1420 is preferably used for interactive games, used for interactive fitness programs and stand alone interaction between a heart rate monitor ("HRM") and the TV/Internet system to view heart rate ("HR") to work out to apps and to store data. The HRM simply outputs HR and accelerometer data to the TV platform where a HRM software (an application software) is processed by the powerful PC-TV computer. All heavy lifting and memory previously performed on board of the monitoring device 20 is preferably performed by the processor 1435 of the computer 1420. The "off-board" processing preferably reduces the cost, size and power requirements of the monitoring device 20 and allows for the more powerful offboard processing, display and storage of HR data by the TV/PC itself. Possible software applications include a pure fitness app, a WEIGHT WATCHERS application, an interactive game or a medical application for in home use. One example of an interactive game requires the player to reach a heart rate of a predetermined target before being able to conduct a specified in-game action. For example, a player has to restore heart rate to a resting baseline before being able to do a high jump. Similarly, the player has to enter a higher target heart zone to "power up" for an attack. HRM application for video game overview: A heart rate monitor is used as an integral, interactive element of video games to add a degree of realism. A basic example is a game that requires shooting skills and skills enhanced or degraded by a physical state as indicated by heart rate level. A players normal heart rate is measured and entered into a game data base. This average is used as a baseline to provide more accurate shooting or combat skills if the heart rate is at a lower level during the activity and accuracy is degraded if the HR is at a certain level above the average. This is reflective of the real world where actual snipers use heart rate as a means to achieve better accuracy. It also is reflective of the real world where a person has to physically move and evade and then fire accurately or engage in other physical combat using manual weapons or personal combat skills. This technique is also used in sports games where shot accuracy is improved by a lower heart rate or conversely adversely affected by an elevate HR reflecting a nervous or agitated state. The game encourages and promotes the use of interactive biofeedback to control the heart rate and improve performance. In this case the biofeedback training translates into real world applications for sports or other activities. The communications from the heart rate monitor to the video monitor displaying the games is preferably accomplished by using a part 15 low power short range radio, standard BLUETOOTH or BLUETOOTH Low Energy to conserve power or other low power short range communications means.

Data is displayed or used simultaneously for interactive exercise or multiple user game programs such as WORLD OF WARCRAFT. Data is alternatively reviewed by individual users or other parties such as a gym teacher or fitness expert.

Those skilled in the art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for a playing an online interactive video game, the system comprising:
   a computer for playing an online interactive video game, the computer comprising a short range wireless transceiver, a processor and a display screen; and
   a monitoring device for monitoring at least a real-time heart rate of the player, the monitoring device in wireless communication with the short range wireless transceiver of the computer to allow the real-time heart rate of the player to be utilized in the interactive video game, the monitoring device comprising an article having an interior surface and an exterior surface, a processor disposed within the article, an optical sensor positioned on the interior surface of the article, the optical sensor measuring blood flow through an artery of an arm of the player, a motion sensor disposed within the article, a wireless transceiver for transmitting information from the monitoring device to the short range wireless transceiver of the computer, the motion sensor and the optical sensor electrically connected to the processor, the processor configured to determine the real-time heart rate of the player based on the blood flow through the artery of the player and the processor configured to detect motion of the player based on a signal from the motion sensor, the optical sensor comprising a LED and a photodetector, and a power source for providing power to the processor, the optical sensor and the motion sensor;
   wherein the processor determines a real-time heart rate of the user by generating a first heart rate value from a first filtered pulse data value which is generated from subtracting an average value of a second set of sample data values from an average value of a first set of sample data values, and wherein the processor uses a cascade adaptive resonant filter to generate subsequent heart rate values;
   wherein an activity of the representation of the player on the display screen of the computer is partially controlled by the real-time heart rate of the player monitored by the optical sensor and the motion of the player detected by the motion sensor.

2. The system according to claim wherein the short range wireless transceiver operates on a communication protocol using a 9 kHz communication format, a 125 kHz RFID communication format, a 13.56 MHz communication format, a 433 MHz communication format, a 433 MHz RFID communication format, or a 900 MHz RFID communication format.

* * * * *